(12) United States Patent
Moriyama et al.

(10) Patent No.: US 9,816,930 B2
(45) Date of Patent: Nov. 14, 2017

(54) IMAGING A TARGET FLUOROPHORE IN A BIOLOGICAL MATERIAL IN THE PRESENCE OF AUTOFLUORESCENCE

(71) Applicant: NOVADAQ TECHNOLOGIES INC., Mississauga (CA)

(72) Inventors: Eduardo Hiroyuki Moriyama, Richmond (CA); Chun Ho Sze, Coquitlam (CA)

(*) Notice: Subject to any disclaimer, the term of this patent is extended or adjusted under 35 U.S.C. 154(b) by 0 days.

(21) Appl. No.: 14/868,369

(22) Filed: Sep. 28, 2015

(65) Prior Publication Data

US 2016/0110870 A1     Apr. 21, 2016

Related U.S. Application Data

(60) Provisional application No. 62/056,830, filed on Sep. 29, 2014.

(51) Int. Cl.
  *G06K 9/00* (2006.01)
  *G01N 21/64* (2006.01)
  (Continued)

(52) U.S. Cl.
  CPC ..... *G01N 21/6456* (2013.01); *G01N 21/6428* (2013.01); *G06T 5/50* (2013.01);
  (Continued)

(58) Field of Classification Search
  CPC .......... G01N 21/6428; G01N 21/6456; G01N 2021/6419; G01N 2021/6439;
  (Continued)

(56) References Cited

U.S. PATENT DOCUMENTS

| 4,109,647 A | 8/1978 | Stern et al. |
| 4,162,405 A | 7/1979 | Chance et al. |

(Continued)

FOREIGN PATENT DOCUMENTS

| AT | 409451 B | 8/2002 |
| CA | 2212257 A1 | 8/1996 |

(Continued)

OTHER PUBLICATIONS

Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience Methods* 45(1-2):15-22.

(Continued)

*Primary Examiner* — Tom Y Lu
(74) *Attorney, Agent, or Firm* — Morrison & Foerster, LLP

(57) ABSTRACT

Methods and systems are disclosed for extracting an image of a target fluorophore in a biological material, which involve inducing both autofluorescence of the biological material and fluorescence of the fluorophore, acquiring an image arising from both the autofluorescence of the biological material and the fluorophore, and an image arising only from the autofluorescence, subtracting the two images to produce an image representing only the fluorophore, wherein relative intensities of the excitation light used to induce the autofluorescence and the fluorescence are modulated prior to acquiring the images.

36 Claims, 9 Drawing Sheets
(2 of 9 Drawing Sheet(s) Filed in Color)

(51) Int. Cl.
  *G06T 5/50* (2006.01)
  *G06T 7/00* (2017.01)
(52) U.S. Cl.
  CPC .... *G06T 7/0016* (2013.01); *G01N 2021/6419* (2013.01); *G01N 2021/6439* (2013.01); *G06T 2207/10064* (2013.01); *G06T 2207/10152* (2013.01); *G06T 2207/20224* (2013.01); *G06T 2207/30024* (2013.01)
(58) Field of Classification Search
  CPC .. G01N 2201/0612; G06T 2207/10064; G06T 2207/20224; G06T 2207/30024; G06T 2207/10152; G06T 5/50; G06T 7/0012; G06T 7/0016; G06T 7/0038
  See application file for complete search history.

(56) References Cited

U.S. PATENT DOCUMENTS

| | | |
|---|---|---|
| 4,200,801 A | 4/1980 | Schuresko |
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 7/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A * | 4/1998 | Hemstreet, III ..... G01N 33/574 435/6.14 |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imaizumi et al. |
| 6,319,273 B1 | 11/2001 | Cheen et al. |

(56) References Cited

U.S. PATENT DOCUMENTS

| | | |
|---|---|---|
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,129,366 B2 | 9/2015 | Nahm et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,610,021 B2 | 4/2017 | Dvorsky et al. |
| 2002/0025541 A1 | 2/2002 | Nelson et al. |
| 2002/0038120 A1 | 3/2002 | Duhaylongsod et al. |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 | 10/2003 | Kaneko et al. |
| 2003/0232016 A1 | 12/2003 | Heinrich |
| 2003/0236458 A1 | 12/2003 | Hochman |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1* | 6/2006 | Levenson ............ A61B 5/0059 250/559.3 |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0319309 A1 | 12/2008 | Bredno et al. |
| 2009/0005693 A1 | 1/2009 | Brauner et al. |
| 2009/0042179 A1* | 2/2009 | Peltie .................. A61B 1/0638 435/4 |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0252682 A1* | 10/2009 | Hillman ............... A61B 5/0059 424/9.1 |
| 2009/0297004 A1 | 12/2009 | Baumgart |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0222673 A1 | 9/2010 | Mangat et al. |
| 2010/0286529 A1 | 11/2010 | Carroll et al. |
| 2011/0001061 A1* | 1/2011 | Ishihara ............ A61B 1/00009 250/458.1 |
| 2011/0013002 A1 | 1/2011 | Thompson et al. |
| 2011/0063427 A1 | 3/2011 | Fengler et al. |
| 2011/0098685 A1 | 4/2011 | Flower |
| 2011/0306877 A1 | 12/2011 | Dvorsky et al. |
| 2012/0078093 A1 | 3/2012 | Flower |
| 2012/0165662 A1 | 6/2012 | Nahm et al. |
| 2013/0230866 A1* | 9/2013 | Miyashita .......... G01N 21/6428 435/7.23 |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0345560 A1 | 12/2013 | Ferguson, Jr. et al. |
| 2014/0099007 A1* | 4/2014 | Sarkar .................... G06T 5/003 382/128 |
| 2014/0308656 A1 | 10/2014 | Flower |
| 2014/0316262 A1 | 10/2014 | Havens |
| 2015/0112192 A1 | 4/2015 | Docherty et al. |
| 2015/0112193 A1 | 4/2015 | Docherty et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |

(56) References Cited

U.S. PATENT DOCUMENTS

| | | | |
|---|---|---|---|
| 2016/0199515 A1 | 7/2016 | Flower | |
| 2016/0371834 A1* | 12/2016 | Watanabe | G06T 7/33 |
| 2017/0039710 A1* | 2/2017 | Minai | A61B 1/00009 |

FOREIGN PATENT DOCUMENTS

| | | |
|---|---|---|
| CA | 2413033 A1 | 3/2000 |
| CN | 1049781 A | 3/1991 |
| CN | 1200174 A | 11/1998 |
| CN | 1399528 A | 2/2003 |
| DE | 3906860 A1 | 9/1989 |
| DE | 19608027 A1 | 9/1996 |
| DE | 10120980 A1 | 11/2002 |
| DE | 69727220 T2 | 12/2004 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0826335 A1 | 3/1998 |
| EP | 1761171 | 3/2007 |
| EP | 1874181 | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-503480 A | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2002-219129 A | 8/2002 |
| JP | 2003-510121 A | 3/2003 |
| JP | 2003-144401 A | 5/2003 |
| JP | 2004-528917 A | 9/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-525126 A | 7/2008 |
| JP | 2008-535600 A | 9/2008 |
| JP | 2008-231113 A | 10/2008 |
| JP | 2010-505582 A | 2/2010 |
| JP | 2011-509768 A | 3/2011 |
| JP | 5918532 B2 | 5/2016 |
| KR | 90-0005434 B1 | 7/1990 |
| KR | 2002-0064287 A | 8/2002 |
| RU | 2288633 C1 | 12/2006 |
| WO | WO-86/02730 A1 | 5/1986 |
| WO | WO-90/10219 A1 | 9/1990 |
| WO | WO-90/12536 A1 | 11/1990 |
| WO | WO-93/25141 A1 | 12/1993 |
| WO | WO-94/12092 A1 | 6/1994 |
| WO | WO-95/00171 A1 | 1/1995 |
| WO | WO-95/26673 A2 | 10/1995 |
| WO | WO-96/09435 A1 | 3/1996 |
| WO | WO-96/09792 A1 | 4/1996 |
| WO | WO-96/18415 A1 | 6/1996 |
| WO | WO-96/23524 A1 | 8/1996 |
| WO | WO-96/39925 A1 | 12/1996 |
| WO | WO-97/08538 A1 | 3/1997 |
| WO | WO-98/24360 A1 | 6/1998 |
| WO | WO-98/30144 A1 | 7/1998 |
| WO | WO-98/46122 A1 | 10/1998 |
| WO | WO-99/00053 A1 | 1/1999 |
| WO | WO-99/47940 A1 | 9/1999 |
| WO | WO-99/53832 A1 | 10/1999 |
| WO | WO-00/42910 A1 | 7/2000 |
| WO | WO-00/47107 A1 | 8/2000 |
| WO | WO-01/08552 A1 | 2/2001 |
| WO | WO-01/17561 A1 | 3/2001 |
| WO | WO-01/22870 A1 | 4/2001 |
| WO | WO-01/39764 A2 | 6/2001 |
| WO | WO-01/69244 A2 | 9/2001 |
| WO | WO-01/80734 A1 | 11/2001 |
| WO | WO-01/82786 A2 | 11/2001 |
| WO | WO-02/061390 A2 | 8/2002 |
| WO | WO-03/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/044822 A1 | 4/2008 |
| WO | WO-2008/070269 A2 | 6/2008 |
| WO | WO-2008/070269 A3 | 6/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |

OTHER PUBLICATIONS

Alander, J.T. et al. (Jan. 1, 2012). "A Review of Indocyanine Green Fluorescent Imaging in Surgery," *International Journal of Biomedical Imaging* 2012:1-26, article ID 940585.

Alfano et al. (Oct. 1987). "Fluorescence Spectra from Cancerous and Normal Human Breast and Lung Tissues," *IEEE Journal of Quantum Electronics* QE-23(10):1806-1811.

Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including Flow Determinations in Brain and Some Other Tissues," *Experimental Eye Research* 15(1):15-29.

Alonso-Burgos, A. et al. (2006). "Preoperative planning of deep inferior epigastric artery perforator flap reconstruction with multislice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation

(56) References Cited

OTHER PUBLICATIONS of Carbonic Anhydrase and Dextran," *Biotechnology and Applied Biochemistry* 23(2) :173-179.
Ancalmo, N. et al. (1997). "Minimally invasive coronary artery bypass surgery: really minimal?" *Ann. Thorac. Surg.* 64:928-929.
Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques*, T. J. Dougherty (Ed.), The Society of Photo-optical Instrumentation Engineers (SPIE) 1426:31-43, fourteen pages.
Andersson-Engels, S. et al. (Mar. 1989). "Tissue Diagnostics Using Laser-Induced Fluorescence," *Berichte der Bunsengesellschaft für physikalische Chemie* 93(3):335-342.
Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.
Annese, V. et al. (2005). "Erthrocytes-Mediated Delivery of Dexamethasone in Steroid-Dependent IBD Patients—a Pilot Uncontrolled Study," *American Journal of Gastroenterol.* 100:1370-1375.
Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.
Author Unknown. (Jun. 4, 2008)."Invitrogen," Material Safety Data Sheet, p. 1-4.
Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.
Azuma, R. et al. (2008, presented in part Jun. 2007). "Detection of Skin Perforators by Indocyanine Green Fluorescence Nearly Infrared Angiography," *PRS Journal* 122(4)1062-1067.
Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.
Barton, J.K. et al. (1999) "Simultaneous irradiation and imaging of blood vessels during pulsed laser delivery," *Lasers in Surgery and Medicine* 24(3):236-243.
Bassingthwaighte, J.B. et al. (Apr. 1974). "Organ Blood Flow, Wash-in, Washout, and Clearance of Nutrients and Metabolites," *Mayo Clin. Proc.* 49(4):248-255.
Batliwala, H. et al. (Apr. 15, 1995). "Methane-Induced Haemolysis of Human Erythrocytes," *Biochemical J.* 307(2):433-438.
Bek, T. (1999). "Diabetic Maculopathy Caused by Disturbances in Retinal Vasomotion: A New Hypothesis," *Acta Ophthalmologica Scandinavica* 77:376-380.
Benson, R.C. et al. (1978). "Fluorescence Properties of Indocyanine Green as Related to Angiography," *Phys. Med. Biol.* 23(1):159-163.
Black's Medical Dictionary, "Perfusion," 42nd Edition (2009), two pages.
Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.
Boldt, .J. et al. (Feb. 1990). "Lung management during cardiopulmonary bypass: influence on extravascular lung water," *Journal of Cardiothoracic Anesthesia* 4(1) :73-79.
Boldt, J. et al. (1991). "Does the technique of cardiopulmonary bypass affect lung water content?" *European Journal of Cardio-Thoracic Surgery* 5:22-26.
Butter, A. et al. (May 2005). "Melanoma in Children and the Use of Sentinel Lymph Node Biopsy," *Journal of Pediatric Surgery* 40(5):797-800.
C2741, Compact High Performance video camera for industrial applications with Built-in contrast enhancement circuit, Jun. 1998.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.
Coffey, J.H. et al. (1984). "Evaluation of Visual Acuity During Laser Photoradiation Therapy of Cancer," *Lasers in Surgery and Medicine* 4(1):65-71.
Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.
Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.
Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.
Dail, W.G. et al. (Oct. 1999). "Multiple Vasodilator Pathways from the Pelvic Plexus to the Penis of the Rat," *International Journal of Impotence Research* 11(5):277-285.
Dan, A.G. et al. (Nov. 2004). "1% Lymphazurin vs 10% Fluorescein for Sentinel Node Mapping in Colorectal Tumors," *Arch Surg.* 139(11):1180-1184.
Daniels, G. et al. (Apr. 2007). "Towards Universal Red Blood Cell," *Nature Biotechnology* 25(4):427-428.
De Flora, A. (Sep. 1986). "Encapsulation of Adriamycin in human erythrocytes," *Proc. Natl. Acad. Sci., USA* 83(18):7029-7033.
De-Grand, A.M. et al. (Dec. 2003). "An Operational Near Infrared Fluorescence Imaging System Prototype for Large Animal Surgery," *Technology in Cancer Research & Treatment* 2(6) :1 -10.
Deloach, J.R. (ed.) et al. (1985). *Red Blood Cells as Carriers for Drugs. A Method for Disseminating Chemotherapeutics, Hormones, Enzymes and Other Therapeutic Agents via The Circulatory System*, Karger, Basel, CH, pp. v-vii, (Table of Contents).
Deloach, J.R. (Jun. 1983). "Encapsulation of Exogenous Agents in Erythrocytes and the Circulating Survival of Carrier Erythrocytes," *Journal of Applied Biochemistry* 5(3):149-157.
Demos (May/Jun. 2004). "Near-Infrared Autofluorescence Imaging for Detection of Cancer," *Journal of Biomedical Optics* 9(3):587-592.
Desai, N.D. et al. (Oct. 18, 2005, e-published on Sep. 28, 2005) "Improving the Quality of Coronary Bypass Surgery with lntraoperative Angiography," *Journal of the American College of Cardiology* 46(8):1521-1525.
Detter, C. et al. (Aug. 1, 2007). "Fluorescent Cardiac Imaging: A Novel lntraoperative Method for Quantitative Assessment of Myocardial Perfusion During Graded Coronary Artery Stenosis," *Circulation* 116(9):1007-1014.
Detter, C. et al. (Jun. 2011). "Near-Infrared Fluorescence Coronary Angiography: A New Noninvasive Technology for lntraoperative Graft Patency Control." *The Heart Surgery Forum* #2001-6973 5(4):364-369.
Dietz, F.B. et al. (Feb. 2003). "Indocyanine Green: Evidence of Neurotoxicity in Spinal Root Axons," *Anesthesiology* 98(2):516-520.
Digital CCD Microscopy (date unknown). Chapter 14, pp. 259-282.
Dougherty, T.J. et al. (1990). "Cutaneous Phototoxic Occurrences in Patients Receiving Photofrin," *Lasers in Surgery and Medicine* 10(5):485-488.
Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, nine pages.
Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.
Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.
Emery R.W. et al. (Aug. 1996). "Revascularization Using Angioplasty and Minimally Invasive Techniques Documented by Thermal Imaging," *The Annals of Thoracic Surgery* 62(2):591-593.

(56) References Cited

OTHER PUBLICATIONS

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Dec. 1973). "Injection Technique for Indocyanine Green and Sodium Fluorescein Dye Angiography of the Eye," *Investigative Opthamology* 12(12):881-895.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.

Frangion I, J.V. (Oct. 2003). "In Vivo Near-Infrared Fluorescence Imaging," *Current Opinion in Chemical Biology* 7(5):626-634.

Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.

Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.

Gagnon, A.R. et al.(2006). "Deep and Superficial Inferior Epigastric Artery Perforator Flaps," , *Cirugia Plástica Ibero-Latinoamericana* 32(4):7-13.

Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.

Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.

Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html>> HTML on Jun. 30, 2014.

Glover, J.C. et al. (Nov. 1986). "Fluorescent Dextran-Amines Used as Axonal Tracers in the Nervous System of the Chicken Embryo," *Journal of Neuroscience Methods* 18(3):243-254.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Haglund, M. et al. (Feb. 1996). "Enhanced Optical Imaging of Human Gliomas and Tumor Margins," *Neurosurgery* 38(2):308-317.

Haglund, M.M. et al. (Nov. 1994). "Enhanced Optical Imaging of Rat Gliomas and Tumor Margins," *Neurosurgery* 35(5):930-941.

Hallock, G.G. (Jul. 2003). "Doppler sonography and color duplex imaging for planning a perforator flap," *Clinics in Plastic Surgery* 30(3):347-357.

Hamamatsu Brochure. (May 1997). Specifications for Real-time Microscope Image Processing System: ARGUS-20 with C2400-75i.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

Hayata, Y. et al. (Jul. 1982). "Fiberoptic Bronchoscopic Laser Photoradiation for Tumor Localization in Lung Cancer," *Chest* 82(1):10-14.

He, Z. (Feb. 2009). "Fluorogold Induces Persistent Neurological Deficits and Circling Behavior in Mice Over-Expressing Human Mutant Tau," *Current Neurovascular Research* 6(1):54-61.

Herts, B.R. (May 2003). "Imaging for Renal Tumors," *Current Opin. Urol.* 13(3):181-186.

Hirano et al. (1989). "Photodynamic Cancer Diagnosis and Treatment System Consisting of Pulse Lasers and an Endoscopic Spectro-Image Analyzer," *Laser in Life Sciences* 3(2):99-116.

Holm, C. et al. (2002). "Monitoring Free Flaps Using Laser-Induced Fluorescence of Indocyanine Green: A Preliminary Experience," *Microsurgery* 22(7):278-287.

Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.

Holm, C. et al. (Dec. 1, 2002). "Intraoperative Evaluation of Skin-Flap Viability Using Laser-Induced Fluorescence of Indocyanine Green", *British Journal of Plastic Surgery* 55(8):635-644.

Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.

Hung, J. et al. (1991). "Autofluorescence of Normal and Malignant Bronchial Tissue," *Lasers in Surgery and Medicine* 11(2) :99-105.

Ikeda, S. (Jul. 1989). "Bronichial Telivision Endoscopy," *Chest* 96(1):41S-42S.

Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.

Jagoe, J.R. et al. (1989). "Quantification of retinal damage during cardiopulmonary bypass," Third International Conference on Image Processing and its Applications (Conf. Publ. No. 307), IEE, pp. 319-323.

(56) References Cited

OTHER PUBLICATIONS

Jamis-Dow, C.A. et al. (Mar. 1996). "Small (< or = 3-cm) Renal Masses: Detection with CT versus US and Pathologic Correlation," *Radiology* 198(3):785-788.

Jolion, J. et al. (Aug. 1991). "Robust Clustering with Applications in Computer Vision," *IEEE Transactions on Pattern Analysis and Machine Intelligence* 13(8):791-802.

Kamolz, L.-P. et al. (Dec. 2003). "Indocyanine Green Video Angiographies Help to Identify Burns Requiring Operation," *Burns* 29(8):785-791.

Kapadia, C.R. et al. (Jul. 1990). "Laser-Induced Fluorescence Spectroscopy of Human Colonic Mucosa. Detection of Adenomatous Transformation," *Gastroenterology* 99(1):150-157.

Kato, H. et al. (Jun. 1985). "Early Detection of Lung Cancer by Means of Hematoporphyrin Derivative Fluorescence and Laser Photoradiation," *Clinics in Chest Medicine* 6(2):237-253.

Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.

Keon, W.J. et al. (Dec. 1979). "Coronary Endarterectomy: An Adjunct to Coronary Artery Bypass Grafting," *Surgery* 86(6):859-867.

Kim, S. et al. (2004, e-published Dec. 7, 2003). "Near-Infrared Fluorescent Type II Quantum Dots for Sentinel Lymph Node Mapping," *Nature Biotechnology* 22(1):93-97.

Kiryu, J. et al. (Sep. 1994). "Noninvasive Visualization of the Choriocapillaris and its Dynamic Filling," *Investigative Ophthalmology & Visual Science* 35(10):3724-3731.

Kitai, T. et al. (Jul. 2005). "Fluorescence Navigation with Indocyanine Green for Detecting Sentinel Lymph Nodes in Breast Cancer," *Breast Cancer* 12(3):211-215.

Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.

Köbbert, C. et al. (Nov. 2000). "Current Concepts in Neuroanatomical Tracing," *Progress in Neurobiology* 62(4):327-351.

Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan. (Abstract only).

Kömürcü, F. et al. (Feb. 2005). "Management Strategies for Peripheral Iatrogenic Nerve Lesions," *Annals of Plastic Surgery* 54(2):135-139.

Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.

Kuipers, J.A. et al. (1999). "Recirculatory and Compartmental Pharmacokinetic Modeling of Alfentanil Pigs, the Influence of Cardiac Output," *Anesthesiology* 90(4):1146-1157.

Kupriyanov, V.V. et al. (Nov. 2004). "Mapping Regional Oxygenation and Flow in Pig Hearts In Vivo Using Near-infrared Spectroscopic Imaging," *Journal of Molecular and Cellular Cardiology* 37(5):947-957.

Kurihara, K. et al. (Jun. 1984). "Nerve Staining with Leucomethylene Blue: An Experimental Study," *Plastic and Reconstruction Surgery* 73(6):960-964.

Kyo, S. "Use of Ultrasound Cardiology during Coronary Artery Bypass Surgery," *Heart and Blood Vessel Imaging II*.

Lam, S. et al. (1991). "Mechanism of Detection of Early Lung Cancer by Ratio Fluorometry," *Lasers in Life Sciences* 4(2):67-73.

Lam, S. et al. (Feb. 1990). "Detection of Early Lung Cancer Using Low Dose Photofrin II," *Chest* 97(2):333-337.

Lam, S. et al. (Jul. 1, 1990). "Detection of Lung Cancer by Ratio Fluorometry With and Without Photofrin II," *Proc. SPIE—Optical Fibers in Medicine V* 1201:561-568.

Lam, S. et al. (Nov. 1-4, 1990). "Fluorescence Imaging of Early Lung Cancer," *Annual International Conference of the IEEE Engineering in Medicine and Biology Society* 12(3):1142-1143.

Lam, S.C. et al. (1993). "Fluorescence Detection," Chapter 20 in *Lung Cancer*, Roth, J.A.(ed.), et al., Blackwell Scientific Publications Inc., 238 Main Street, Cambridge, Massachusetts, 02142, pp. 325-338, sixteen pages.

Lanciego, J.L. et al. (Jun. 1998). "Multiple Neuroanatomical Tracing in Primates," *Brain Research Protocols* 2(4):323-332.

Lanciego, J.L. et al. (Oct. 1998). "Multiple Axonal Tracing: Simultaneous Detection of Three Tracers in the Same Section," *Histochemistry and Cell Biology* 110(5):509-515.

Laub, G.W. et al. (Nov. /Dec. 1989). "Experimental Use of Fluorescein for Visualization of Coronary Arteries," *Vascular and Endovascular Surgery* 23(6):454-457.

Lee, E.T. et al. (Mar. 1997). "A New Method for Assessment of Changes in Retinal Blood Flow," *Medical Engineering & Physics* 19(2):125-130.

Leissner, J. et al. (Jan. 2004). "Extended Radical Lymphadenectomy in Patients with Urothelial Bladder Cancer: Results of a Prospective Multicenter Study," *The Journal of Urology* 171(1):139-144.

Leithner, "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/dissertationen/leith nerch ristoph-2003-07-14/> [English Abstract and Machine Translation].

Liedberg et al. (2003). "Sentinel-Node-Diagnostik Beim Invasiven (Bladder Cancer and the Sentinel Node Concept)," *Aktuel Urol.* 34:115-118 (English Abstract Only).

Liedberg, F. et al. (Jan. 2006). "Intraoperative Sentinel Node Detection Improves Nodal Staging in Invasive Bladder Cancer," *The Journal of Urology* 175(1):84-89.

Lippincott's New Medical Dictionary. "Perfusion," p. 707 (1897), three pages.

Liptay, M.J. (Mar. 2004). "Sentinel Node Mapping in Lung Cancer," *Annals of Surgical Oncology* 11(Supplement 3):271S-274S.

Liu Q. P. et al. (Apr. 2007). "Bacterial Glycosidases for the Production of Universal Red Blood Cells" *Nature Biotechnology* 25(7):454-464.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3)1055-1059.

Magnani, M. et al. (Aug. 1998). "Erythrocyte Engineering for Drug Delivery and Targeting," *Biotechnology and Applied Biochemistry* 28(Part 1):1-6.

Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.

May, S. (May/Jun. 1995). "Photonic Approaches to Burn Diagnostics," *Biophotonics International* pp. 44-50.

McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

(56) References Cited

OTHER PUBLICATIONS

Merriam Webster Medline Plus Medical Dictionary. "Perfusion," located at http://www.merriam-webster.com/medlineplus/perfusion, last visited on Apr. 15, 2015, one page.
Microscope Video Camera, For Fluorescent Observation, Easy Fluorescent Image Analysis a CCD Camera.
Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.
Mitaka USA, Inc. (2015). "PDE Breast Free Flap Evaluation," located at <http://mitakausa.com/category/pde_education/flaps/>, last visited on Dec. 29, 2015, four pages.
Mitaka USA, Inc. (2015). "PDE-Neo" located at <http://mitakausa.com/pde-neo/>, last visited on Dec. 29, 2015, two pages.
Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.
Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.
Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-24.
Motomura et al. (1999). "Sentinel Node Biopsy Guided by Indocyanine Green Dye in Breast Cancer Patients," *Japan J. Clin. Oncol.* 29(12):604-607.
Mullooly, V.M. et al. (1990). "Dihematoporphyrin Ether-Induced Photosensitivity in Laryngeal Papilloma Patients," *Lasers in Surgery and Medicine* 10(4):349-356.
Murphy (2001). "Digital CCD Microscopy," Chapter 14 in *Fundamentals of Light Microscopy and Electronic Imaging*, John Wiley and Sons, pp. i-xi and 259-281.
Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.
Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366.
Nakayama, A. et al. (Oct. 2002). "Functional Near-Infrared Fluorescence Imaging for Cardiac Surgery and Targeted Gene Therapy," *Molecular Imaging* 1(4):365-377.
Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.
Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.
Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.
Novadaq Technologies Inc. (Jan 29, 2007). "Novadaq Imaging System Receives FDA Clearance for use During Plastic Reconstructive Surgery," *PR Newswire* three pages.
Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.
Ogata, F. et al. (Jun. 2007). "Novel Lymphography Using Indocyanine Green Dye for Near-Infrared Fluorescence Labeling," *Annals of Plastic Surgery* 58(6):652-655.

Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.
Ooyama, M. (Oct. 12-15, 1994). The 8th Congress of International YAG Laser Symposium, The 15th Annual Meeting of Japan Society for Laser Medicine, Sun Royal Hotel, Japan.
Ott, P. (198). "Hepatic Elimination of Indocyanine Green with Special Reference to Distribution Kinetics and the Influence of Plasma Protein Binding," *Pharmacology & Toxicology* 83(Supp. II):5-48.
Oxford Concise Medical Dictionary. "Perfusion," p. 571 (1980), three pages.
Pagni, S. et al. (Jun. 1997). "Anastomotic Complications in Minimally Invasive Coronary Bypass Grafting," *Ann. Thorac. Surg.* 63(6 Suppl):S64-S67.
Palcic et al. (1991). "Lung Imaging Fluorescence Endoscope: A Device for Detection of Occult Lung Cancer," *Medical Design and Material*, thirteen pages.
Palcic, B. et al. (1990). "Development of a Lung Imaging Fluorescence Endoscope," *Annual International Conference of the IEEE Engineering in Medicine and Biology Society* 12(1):0196-0197.
Palcic, B. et al. (Aug. 1, 1990). "The Importance of Image Quality for Computing Texture Features in Biomedical Specimens," *Proc. SPIE* 1205:155-162.
Palcic, B. et al. (Jun. 1, 1991). "Lung Imaging Fluorescence Endoscope: Development and Experimental Prototype," *Proc. SPIE* 1448:113-117.
Palcic, B. et al. (Mar. 1991). "Detection and Localization of Early Lung Cancer by Imaging Techniques," *Chest* 99(3):742-743.
Pandharlpande, P.V. et al. (Mar. 2005). "Perfusion Imaging of the Liver: Current Challenges and Future Goals," *Radiology* 234(3):661-673.
Paques, M. et al. (Mar. 2003). "Axon-Tracing Properties of Indocyanine Green," *Arch Ophthalmol.* 121(3):367-370.
Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.
Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.
Peak, M.J. et al. (1986). "DNA-to-Protein Crosslinks and Backbone Breaks Caused by FAR- and NEAR-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.
Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (Abstract only).
Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707, last visited on Oct. 7, 2016, two pages.
Perez, M.T. et al. (Sep. 2002). "In Vivo Studies on Mouse Erythrocytes Linked to Transferrin," *IUBMB Life* 54(3):115-121.
Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).
Phillips, R.P. et al. (1991). "Quantification of Diabetic Maculopathy by Digital Imaging of the Fundus," *Eye* 5(1):130-137.
Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.
Profio, a.E. et al. (Jul.-Aug. 1984). "Fluorometer for Endoscopic Diagnosis of Tumors," *Medical Physics* 11(4):516-520.
Profio, A.E. et al. (Jun. 1, 1991). "Endoscopic Fluorescence Detection of Early Lung Cancer," *Proc. SPIE* 1426:44-46.

(56) References Cited

OTHER PUBLICATIONS

Profio, A.E. et al. (Nov./Dec. 1979). "Laser Fluorescence Bronchoscope for Localization of Occult Lung Tumors," *Medical Physics* 6:523-525.
Profio, A.E. et al. (Sep.-Oct. 1986). "Digital Background Subtraction for Fluorescence Imaging," *Medical Physics* 13(5):717-721.
Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.
Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.
Raabe et al. (2009, e-published on Nov. 12, 2008). "Laser Doppler Imaging for Intraoperative Human Brain Mapping", *NeuroImage* 44:1284-1289.
Raabe, A. et al. (Jan. 2003). "Near-Infrared Indocyanine Green Video Angiography: A New Method for Intraoperative Assessment of Vascular Flow," *Neurosurgery* 52(1):132-139.
Rava, R.P. et al. (Jun. 1, 1991). "Early Detection of Dysplasia in Colon and Bladder Tissue Using Laser-Induced Fluorescence," *Proc. SPIE* 1426:68-78.
Razum, N. et al. (Nov. 1987). "Skin Photosensitivity: Duration and Intensity Following Intravenous Hematoporphyrin Derivatives, HpD and DHE, " *Photochemistry and Photobiology* 46(5):925-928. Report on Observation by C2400-75i and ARGUS20 Under Low illumination conditions, Jan. 17, 2008.
Request for Invalidation mailed on Jun. 29, 2007 for Japanese Patent No. JP-3881550, filed by Hamamatsu Photonics, Inc. (with English Translation).
Reuthebuch, O et al. (Feb. 2004). "Novadaq SPY: Intraoperative Quality Assessment in Off Pump Coronary Artery Bypass Grafting," *Chest* 125(2):418-424.
Reuthebuch, O.T. et al. (May 2003). "Graft Occlusion After Deployment of the Symmetry Bypass System," *Ann. Thorac. Surg.* 75(5):1626-1629.
Richards-Kortum, R. et al. (Jun. 1991). "Spectroscopic Diagnosis of Colonic Dysplasia: Spectroscopic Analysis," *Biochemistry and Photobiology* 53(6):777-786.
Roberts, W.W. et al. (Dec. 1997). "Laparoscopic Infrared Imaging," *Surg. Endoscopy* 11(12):1221-1223.
Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.
Ropars, C. (ed.) et al. (1987). *Red Blood Cells as Carriers for Drugs. Potential therapeutic Applications*, Pergamon Press, Oxford, New York, pp. v-vii, (Table of Contents only).
Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.
Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.
Rossi, L. et al. (2001). "Erthrocyte-Mediated Delivery of Dexamethasone in Patients with Chronic Obstructive Pulmonary Disease," *Biotechnol. Appl. Biochem.* 33:85-89.
Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.
Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.
Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.
Rubben, A. et al. (Mar. 1994). "Infrared Videoangiofluorography of the Skin with Indocyanine Green—Rat Random Cutaneous Flap Model and Results in Man," *Microvascular Research* 47(2):240-251.
Rubens, F.D. et al. (2002). "A New and Simplified Method for Coronary and Graft Imaging During CABG," *The Heart Surgery Forum* 5(2):141-144.
Sakatani, K. et al. (Nov. 1997). "Noninvasive Optical Imaging of the Subarchnoid Space and Cerebrospinal Fluid Pathways Based on Near Infrared Fluorescence," *J. Neurosurg.* 87(5):738-745.
Salmon, E.D. et al. (Oct. 1994). "High Resolution Multimode Digital Imaging System for Mitosis Studies In Vivo and In Vitro," *Biol. Bull* 187(2):231-232.
Sato, et al., (1991). "Development of a Visualization Method for the Microcirculation of Deep Viscera Using an Infrared Intravital Microscope System," *Research on ME Devices and ME Technology* (with English Translation), five pages.
Satpathy G.R. et al. (Oct. 2004) "Loading Red Blood Cells with Trehalose: A Step Towards Biostabilization," *Cryobiology* 49(2):123-136.
Schaff, H.V. et al. (Oct. 15, 1996). "Minimal Thoracotomy for Coronary Artery Bypass: Value of Immediate Postprocedure Graft Angiography," *Supplement to Circulation* 94(8):1-51, (Abstract No. 0289), two pages.
Schellingerhout, D. et al. (Oct. 2000). "Quantitation of HSV Mass Distribution in a Rodent Brain Tumor Model," *Gene Therapy* 7(19):1648-1655.
Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.
Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.
Schneider Jr., H.C. et al. (Jan. 1975). "Fluorescence of Testicle, an Indication of Viability of Spermatic Cord After Torsion," *Urology* V(1):133-136.
Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.
Sekijima, M. et al. (Sep. 2004). "An Intraoperative Fluorescent Imaging System in Organ Transplantation," *Transplantation Proceedings* 36(7):2188-2190.
Serov, A. et al. (Mar. 1, 2002). "Laser Doppler Perfusion Imaging with a Complimentary Metal Oxide Semiconductor Image Sensor," *Optics Letters* 27(5):300-302.
Serov, A.N. et al. (Sep. 23, 2003). "Quasi-Parallel Laser Doppler Perfusion Imaging Using a CMOS Image Sensor," *Proc. SPIE* 5067:73-84.
Sezgin, M. et al. (Jan. 2004). "Survey Over Image Thresholding Techniques and Quantitative Performance Evaluation," *Journal of Electronic Imaging* 13(1):146-165.
Sherif, A. et al. (Sep. 2001). "Lymphatic Mapping and Detection of Sentinel Nodes in Patients with Bladder Cancer," *The Journal of Urology* 166(3):812-815.
Sheth, S.A. et al. (Apr. 22, 2004)"Linear and Nonlinear Relationships between Neuronal Activity, Oxygen Metabolism, and Hemodynamic Responses," *Neuron* 42(2):347-355.
Shoaib, T. et al. (Jun. 1, 2001). "The Accuracy of Head and Neck Carcinoma Sentinel Lymph Node Biopsy in the Clinically NO Neck," *Cancer* 91(11):2077-2083.
Siemers, B.M. et al. (Nov. 2001). "The Acoustic Advantage of Hunting at Low Heights Above Water: Behavioual Experiments on the European 'Trawling' Bats Myotis Capaccinii, M Dasycneme and M. Daubentonii," *J. Eperimental Biol.* 204(Pt. 22):3843-3854.

(56) References Cited

OTHER PUBLICATIONS

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336, (Abstract only), two pages.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ϵ-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.

Wachi, A. et al. (Apr. 1995). "Characteristics of Cerebrospinal Fluid Circulation in Infants as Detected With MR Velocity Imaging," *Child's Nerv Syst* 11(4):227-230.

Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.

Weinbeer, M. et al. (Nov. 25, 2013). "Behavioral Flexibility of the Trawling Long-Legged Bat, *Macrophyllum macrophyllum* (Phyllostomidae)," *Frontiers in Physiology* 4(Article 342):1-11.

What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.

Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.

Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.

Wollert, H.G. et al. (Dec. 1989). "Intraoperative Visualization of Coronary Artery Fistula Using Medical Dye," *The Thoracic and Cardiovascular Surg.* 46(6):382-383.

Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.

Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

Yamaguchi, S. et al. (Apr. 2005). "Evaluation of Skin Perfusion After Nipple-Sparing Mastectomy by Indocyanine Green Dye" *Journal of Saitama Medical University*, Japan, 32(2):45-50, (With English Abstract).

Yoneya, S. et al. (Jun. 1998). "Binding Properties of Indocyanine Green in Human Blood," *IOVS* 39(7):1286-1290.

Yoneya, S. et al. (Sep. 1993). "Improved Visualization of the Choroidal Circulation with Indocyanine Green Angiography," *Arch Opthalmol.* 111(9):1165-1166.

(56) References Cited

OTHER PUBLICATIONS

Young. I.T. et al. (1993). "Depth of Focus in Microscopy," SCIA '93, Proc. of the 8th Scandinavian Conference on Image Analysis, Tromso, Norway, pp. 493-498, six pages.
Canadian Office Action dated Feb. 27, 2017 for Canadian Application No. 2,750,760, filed on Jul. 25, 2011, three pages.
Canadian Office Action dated Jan. 19, 2017 for Canadian Application No. 2,914,778 filed on Dec. 8, 2015, four pages.
Canadian Office Action dated Mar. 16, 2016, for CA Application No. 2,750,760 filed on Jan. 23, 2009, five pages.
Canadian Office Action dated Oct. 25, 2016 for Canadian Patent Application No. 2,811,847, filed on Sep. 20, 2011, three pages.
Canadian Office Action dated Sep. 30, 2015, for CA Application No. 2,811,847, filed on Sep. 20, 2011, four pages.
Chinese Office Action dated Jul. 3, 2012, issued in counterpart Chinese Application No. 200980123414.0—(with English Translation).
Chinese Office Action dated May 23, 2013, issued in counterpart Chinese Application No. 200980123414.0—(with English Translation).
Chinese Office Action dated Nov. 12, 2015, for Chinese Patent Application No. 201180057244.8, filed on Sep. 20, 2010, five pages, (English Translation).
Chinese Third Office Action dated Aug. 8, 2016 for Chinese Application No. 201180057244.8 filed on Sep. 20, 2011, eighteen pages, (with English Translation).
EP Communication in pursuant to Article 94(3) EPC dated Mar. 9, 2016 for European Patent Application No. 09739980.2 filed May 1, 2009, five pages.
European Communication pursuant to Article 94(3) dated May 27, 2016 for EP Application No. 15160177.0 filed on Aug. 11, 2000, five pages.
European Communication pursuant to Rules 70(2) and 70a(2) EPC in EP Application No. 09732993.2 dated May 15, 2014, one page.
European Communication pursuant to Rules 70(2) and 70a(2) EPC in EP Application No. 16163909.1, dated Nov. 14, 2016, two pages.
European Decision in Opposition Proceeding Revoking (Jun. 10, 2010). European Patent No. 1 143 852, thirty pages.
European Notice of Allowance dated Oct. 21, 2015, for EP Application No. 11 826 475.3, filed on Sep. 20, 2010, eight pages.
European Notice of Allowance dated Oct. 29, 2015, for EP Application No. 09 704 642.9, filed on Jan. 25, 2008, two pages.
European Office Action dated Mar. 27, 2015, for EP Application No. 09 732 993.2, filed on Apr. 14, 2008, six pages.
European Opposition of European Patent No. EP1143852 lodged by Hamamatsu Photonics, Inc., Jul. 30, 2008.
European Summons to attend Oral Proceedings pursuant to Rule 115(1) EPC dated Apr. 25, 2016, for European patent application No. 09732993.2, filed on Apr. 14, 2009, 5 pages.
European Summons to attend Oral Proceedings pursuant to Rule 115(1) EPC dated Dec. 16, 2016, for European patent application No. 15160177.0, filed on Aug. 11, 2000, seven pages.
Extended European Search Report dated Oct. 14, 2015 for EP Application No. 13806313.6 filed on Jun. 20, 2013, nine pages.
Extended European Search Report dated Apr. 28, 2014, for EP Application No. 09 732 993.2, filed on Apr. 14, 2008, eight pages.
Extended European Search Report dated Feb. 22, 2012, for EP Application No. 09 704 642.9, filed on Jan. 25, 2008, fifteen pages.
Extended European Search Report dated Jan. 28, 2014, for EP Application No. 11 826 475.3, filed on Sep. 20, 2010, six pages.
Indian Examination Report dated Sep. 22, 2016 for Indian Application No. 7566/DELNP/2010, filed on Oct. 27, 2010, nine pages.
International Preliminary Examination Report dated Jul. 1, 2001 for PCT/US00/22088, filed on Aug. 11, 2000, three pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report for Application No. PCT/EP2008/008547, dated Jun. 2, 2009; five pages.
International Search Report dated Dec. 3, 2015 for PCT Application No. PCT/CA2015/050973 filed on Sep. 28, 2015, three pages.
International Search report dated Jul. 4, 2008 for International Application No. PCT/US2007/080847, filed on Oct. 9, 2007, three pages.
International Search Report dated Dec. 3, 2009, for PCT Patent Application No. PCT/IB2009/005700, filed on Apr. 14, 2009, three pages.
International Search Report dated Feb. 1, 2012, for PCT Patent Application No. PCT/IB2011/002381, filed on Sep. 20, 2011, five pages.
International Search Report dated Jan. 22, 2014, for PCT Application No. PCT/IB2013/001934, filed on Jun. 20, 2013, four pages.
International Search Report dated Jun. 8, 2009, for PCT Patent Application No. PCT/CA2009/000073, filed on Jan. 23, 2009, three pages.
International Search Report dated Oct. 18, 2000, for PCT Application No. PCT/US2000/22088, filed on Aug. 11, 2000, one page.
International Search Report dated Sep. 11, 2009 for Application No. PCT/US2009/042606 filed on May 1, 2009, five pages.
Japanese First Office Action dated Feb. 1, 2016 for Japanese Patent Application No. 2015-517876 filed Jun. 20, 2013, eight pages, (with English Translation).
Japanese Notice of Allowance dated Sep. 16, 2016, for Japanese Patient Application No. 2015-517876 filed on Jun. 20, 2013, six pages, (with English Translation).
Japanese Office Action dated Jul. 30, 2013, issued in counterpart Japanese Application No. 2011-504574, filed on Apr. 14, 2009, six pages (with English Translation).
Japanese Office Action dated Apr. 1, 2016, for Japanese Patent Application No. 2013-529729, filed on Mar. 21, 2013, seven pages, (with English Translation).
Japanese Office Action dated Sep. 14, 2015, for Japanese Patent Application No. 2011-504574, filed on Apr. 14, 2009, three pages, (English Translation).
Korean Notice of Allowance dated Apr. 29, 2016, for Korean Patent Application No. 10-2010-7024977, filed on Apr. 14, 2009, three pages, (with English Translation).
Korean Office Action dated Nov. 30, 2015, for Korean Patent Application No. 10-2010-7024977, filed on Apr. 14, 2009, two pages, (English Translation).
Korean Patent Office, Office Action dated Jun. 25, 2014 in Korean Patent Application No. 10-2013-7035027, filed on May 14, 2009, fifteen pages, (with English Translation).
Mexican Office Action dated May 30, 2013, issued in counterpart Mexican Application No. MX/a/2010/011249, no translation.
Partial European Search Report dated Dec. 16, 2010 for European Application No. 10186218.3 filed on Aug. 11, 2000, seven pages.
Partial European Search Report dated Jun. 11, 2014 for European Application No. 13178642.8, filed on May 1, 2009, five pages.
Russian Decision on Grant dated Jul. 29, 2013, issued in counterpart Russian Application No. 2011111078.14, five pages (with English Translation).
Russian Office Action dated Mar. 29, 2013, issued in counterpart Russian Application No. 2011111078.14, three pages, (with English Translation).
Supplemental European Search Report dated Jul. 6, 2004 for EP Application No. 00955472.6 filed on Aug. 11, 2000, four pages.
U.S. Final Office Action dated Apr. 10, 2008, for U.S. Appl. No. 11/106,154, filed Apr. 14, 2005, six pages.
U.S. Final Office Action dated Apr. 2, 2013, for U.S. Appl. No. 13/419,368, filed Mar. 13, 2012, five pages.
U.S. Final Office Action dated Apr. 20, 2016, for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012, for U.S. Appl. No. 11/912,877, filed Aug. 13, 2008, ten pages.
U.S. Final Office Action dated Dec. 31, 2015 for U.S. Appl. No. 14/177,050 filed Feb. 10, 2014, eighteen pages.

(56) References Cited

OTHER PUBLICATIONS

U.S. Final Office Action dated Dec. 4, 2014, for U.S. Appl. No. 12/776,835, filed May 10, 2010, thirteen pages.
U.S. Final Office Action dated Feb. 1, 2013, for U.S. Appl. No. 12/776,835, filed May 10, 2010, thirteen pages.
U.S. Final Office Action dated Feb. 13, 2015, for U.S. Appl. No. 14/543,429, filed Nov. 17, 2014, six pages.
U.S. Final Office Action dated Feb. 18, 2010, for U.S. Appl. No. 11/106,154, filed Apr. 14, 2005, six pages.
U.S. Final Office Action dated Feb. 4, 2015 for U.S. Appl. No. 13/314,418, filed Dec. 8, 2011, six pages.
U.S. Final Office Action dated Jul. 21, 2016 for U.S. Appl. No. 14/543,356, filed Nov. 17, 2014, seven pages.
U.S. Final Office Action dated Jul. 9, 2015, for U.S. Appl. No. 14/543,356, filed Nov. 17, 2014, eight pages.
U.S. Final Office Action dated Jun. 1, 2015, for U.S. Appl. No. 14/543,429, filed Nov. 17, 2014, nine pages.
U.S. Final Office Action dated Jun. 13, 2014, for U.S. Appl. No. 12/776,835, filed May 10, 2010, thirteen pages.
U.S. Final Office Action dated Jun. 25, 2014, for U.S. Appl. No. 12/933,477, filed Sep. 20, 2010, fifteen pages.
U.S. Final Office Action dated Mar. 20, 2017, for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013, for U.S. Appl. No. 12/933,477, filed Sep. 20, 2010, twelve pages.
U.S. Final Office Action dated Nov. 6, 2013, for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011, for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015, for U.S. Appl. No. 12/933,477, filed Sep. 20, 2010, six pages.
U.S. Final Office Action dated Sep. 23, 2004, for U.S. Appl. No. 09/744,034, filed Apr. 27, 2001, seven pages.
U.S. Final Office Action dated Sep. 29, 2016, for U.S. Appl. No. 13/922,996, filed Jun. 20, 2013, fourteen pages.
U.S. Non-Final Office Action dated Apr. 1, 2015, for U.S. Appl. No. 12/933,477, filed Sep. 20, 2010, fourteen pages.
U.S. Non-Final Office Action dated Apr. 26, 2012, for U.S. Appl. No. 12/776,835, filed May 10, 2010, nine pages.
U.S. Non-Final Office Action dated Apr. 28, 2010, for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 20, 2013, for U.S. Appl. No. 12/933,477, filed Sep. 20, 2010, thirteen pages.
U.S. Non-Final Office Action dated Dec. 30, 2010, for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016, for U.S. Appl. No. 14/543,356, filed Nov. 17, 2014, seven pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012, for U.S. Appl. No. 11/912,877, filed Aug. 13, 2008, eleven pages.
U.S. Non-Final Office Action dated Jan. 9, 2009, for U.S. Appl. No. 11/106,154, filed Apr. 14, 2005, six pages.
U.S. Non-Final Office Action dated Jul. 2, 2015, for U.S. Appl. No. 14/177,050, filed Feb. 10, 2014, nineteen pages.
U.S. Non-Final Office Action dated Jul. 22, 2015 for U.S. Appl. No. 13/314,418, filed Dec. 8, 2011, six pages.
U.S. Non-Final Office Action dated Jul. 8, 2014 for U.S. Appl. No. 13/314,418, filed Dec. 8, 2011, seven pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 10, 2004, for U.S. Appl. No. 09/744,034, filed Apr. 27, 2001, seven pages.
U.S. Non-Final Office Action dated Mar. 13, 2015, for U.S. Appl. No. 14/543,356, filed Nov. 17, 2014, eight pages.
U.S. Non-Final Office Action dated Mar. 6, 2007, for U.S. Appl. No. 11/106,154, filed Apr. 14, 2005, eight pages.
U.S. Non-Final Office Action dated May 21, 2015, for U.S. Appl. No. 13/922,996, filed Jun. 20, 2013, fourteen pages.
U.S. Non-Final Office Action dated May 6, 2015 for U.S. Appl. No. 12/063,349, filed May 12, 2010, seventeen pages.
U.S. Non-Final Office Action dated Nov. 18, 2016, for U.S. Appl. No. 12/933,477, filed Sep. 20, 2010, six pages.
U.S. Non-Final Office Action dated Nov. 27, 2015, for U.S. Appl. No. 14/543,429, filed Nov. 17, 2014, six pages.
U.S. Non-Final Office Action dated Nov. 9, 2015, for U.S. Appl. No. 14/177,045, filed Feb. 10, 2014, seven pages.
U.S. Non-Final Office Action dated Oct. 12, 2016, for U.S. Appl. No. 14/543,429, filed Nov. 17, 2014, nine pages.
U.S. Non-Final Office Action dated Oct. 28, 2016, for U.S. Appl. No. 14/543,356, filed Nov. 17, 2014, eight pages.
U.S. Non-Final Office Action dated Oct. 3, 2013, for U.S. Appl. No. 12/776,835, filed May 10, 2010, twelve pages.
U.S. Non-Final Office Action dated Sep. 15, 2010, for U.S. Appl. No. 11/106,154, filed Apr. 14, 2005, six pages.
U.S. Non-Final Office Action dated Sep. 30, 2010 for U.S. Appl. No. 11/515,419, filed Sep. 1, 2006, eleven pages.
U.S. Non-Final Office Action dated Sep. 5, 2012 for U.S. Appl. No. 12/933,477, filed Sep. 20, 2010, seven pages.
U.S. Notice of Allowance dated Apr. 17, 2014, for U.S. Appl. No. 13/419,368, filed Mar. 13, 2012, five pages.
U.S. Notice of Allowance dated Aug. 7, 2014, for U.S. Appl. No. 13/850,063, filed Mar. 25, 2013, nine pages.
U.S. Notice of Allowance dated Dec. 2, 2016, for U.S. Appl. No. 14/598,832, filed Jan. 16, 2015, seven pages.
U.S. Notice of Allowance dated Jul. 13, 2016, for U.S. Appl. No. 14/598,832, filed Jan. 16, 2015, seven pages.
U.S. Notice of Allowance dated Mar. 15, 2016, for U.S. Appl. No. 14/598,832, filed Jan. 16, 2015, seven pages.
U.S. Notice of Allowance dated Mar. 7, 2005, for U.S. Appl. No. 09/744,034, filed Apr. 27, 2001, five pages.
U.S. Notice of Allowance dated May 26, 2016, for U.S. Appl. No. 14/177,045, filed Feb. 10, 2014, eight pages.
U.S. Notice of Allowance dated Nov. 25, 2015, for U.S. Appl. No. 14/598,832, filed Jan. 16, 2015, seven pages.
U.S. Notice of Allowance dated Nov. 30, 2010, for U.S. Appl. No. 11/946,672, filed Nov. 28, 2007, six pages.
U.S. Notice of Allowance dated Oct. 16, 2014, for U.S. Appl. No. 13/850,063, filed Mar. 25, 2013, eight pages.
U.S. Notice of Allowance dated Oct. 18, 2012, for U.S. Appl. No. 12/841,659, filed Jul. 22, 2010, seven pages.
U.S. Notice of Allowance dated Oct. 4, 2013, for U.S. Appl. No. 11/912,877, filed Aug. 13, 2008, nine pages.
U.S. Notice of Allowance dated Oct. 6, 2014, for U.S. Appl. No. 13/419,368, filed Mar. 13, 2012, five pages.
Written Opinion for Application No. PCT/EP2008/008547, dated Jun. 2, 2009; eleven pages.
Written Opinion of the International Searching Authority dated Jul. 4, 2008 for International Application No. PCT/US2007/080847, filed on Oct. 9, 2007, six pages.
Written Opinion of the International Searching Authority dated Dec. 3, 2009, for PCT Patent Application No. PCT/IB2009/005700, filed on Apr. 14, 2009, six pages.
Written Opinion of the International Searching Authority dated Dec. 3, 2015 for PCT Application No. PCT/CA2015/050973 filed on Sep. 28, 2015, five pages.

(56) References Cited

OTHER PUBLICATIONS

Written Opinion of the International Searching Authority dated Feb. 1, 2012, for PCT Patent Application No. PCT/IB2011/002381, filed on Sep. 20, 2011, four pages.
Written Opinion of the International Searching Authority dated Jan. 22, 2014, for PCT Application No. PCT/IB2013/001934, filed on Jun. 20, 2013, six pages.
Written Opinion of the International Searching Authority dated Jun. 8, 2009, for PCT Patent Application No. PCT/CA2009/000073, filed on Jan. 23, 2009, four pages.
U.S. Final Office Action dated Apr. 4, 2017, for U.S. Appl. No. 12/933,477, filed Sep. 20, 2010, twelve pages.

* cited by examiner

IMAGING A TARGET FLUOROPHORE IN A BIOLOGICAL MATERIAL IN THE PRESENCE OF AUTOFLUORESCENCE

CROSS-REFERENCE TO RELATED APPLICATION

This application is a non-provisional application that claims the benefits of priority of U.S. Provisional Application No. 62/056,830, filed on Sep. 29, 2014, pending, the disclosure of which is incorporated herein by reference.

TECHNICAL FIELD

The present invention relates generally to fluorescence imaging, and in particular to imaging a target fluorophore in a biological material in the presence of autofluorescence.

BACKGROUND

In the life sciences, fluorescence is typically used as a non-invasive method of identifying and analyzing biological materials. Specific targets in the biological material such as for example, proteins, nucleic acids, lipids, cells and cell components, stem cells or small molecules can be labeled with an extrinsic or exogenous fluorophore, and thus subsequently imaged. Biological materials also naturally fluoresce, which is known as intrinsic fluorescence or "autofluorescence" because it occurs in the absence of exogenously administered fluorophores. Autofluorescence is believed to originate from various endogenous fluorophores in biological materials, including for example nicotinamide adenine dinucleodde (NADH), elastin, collagen, flavins, amino acids and porphyrins.

Autofluorescence and fluorescence emission can be generated and recorded as images when light with the appropriate excitation wavelengths illuminates the biological material. However, autofluorescence, which is the result of a combination of fluorophores and is characterized by broad emission spectra extending over several hundred nanometers, can interfere with the ability to detect the emission of a specific fluorophore, when the emission spectra of the fluorophore and the autofluorescence overlap. In such instances, in addition to reducing signal detection sensitivity by masking the fluorescence of the fluorophore of interest, autofluorescence may also decrease the specificity of detection by providing false positive results.

One approach to addressing this problem is to utilize means to reduce or minimize the detected emission signal that is contributed by autofluorescence of the biological material. The prior art describes methods to reduce autofluorescence by employing various pre-treatments of the biological material prior to image acquisition. However, such techniques may also degrade the quality of the biological material itself, and are typically not suitable for in vivo applications. Alternatively, if the autofluorescence emission itself cannot be mitigated, it is possible to minimize the contribution of signal from autofluorescence to image data by means of digital manipulation of any acquired fluorescence images. For example, in images containing the combined signal from both the fluorophore of interest and autofluorescence, some of these methods rely on acquiring estimates of the "pure" autofluorescence signal and using such estimates to remove autofluorescence by a weighted subtraction. Other methods use statistical correlation techniques to correct for the additive autofluorescence signal. These image data manipulation techniques are described in prior art references and are generally limited by poor accuracy, by the need for small (i.e., low resolution) data sets, or by the need for significant post-processing. It is consequently desirable to establish a high resolution image processing technique to quickly and accurately distinguish the fluorescence emitted by a fluorophore of interest in a biological material from the autofluorescence emission in that same biological material.

SUMMARY

In accordance with one aspect of the invention, there is provided a method for extracting an image of a target fluorophore in a biological material wherein a waveband for the target fluorophore emission overlaps a waveband for autofluorescence emission in the biological material. The method includes illuminating the biological material with a first excitation light to induce a first fluorescence emission arising from both autofluorescence of the biological material and fluorescence of the target fluorophore and with a second excitation light to induce a second fluorescence emission arising from the autofluorescence of the biological material, acquiring a first fluorescence image from the first fluorescence emission and a second fluorescence image from the second fluorescence emission, and processing the first and second fluorescence images to extract a third fluorescence image representing the target fluorophore, wherein relative intensities of the first and second excitation lights are modulated prior to acquiring the first and second fluorescence images. The processing may for example involve subtracting the second fluorescence image from the first fluorescence image.

According to an embodiment, the modulation of the relative intensities includes identifying a wavelength region in the first and second fluorescence emissions, wherein the wavelength region is a region where emission arising from the fluorophore is present in the first fluorescence emission and absent in the second fluorescence emission, selecting a waveband outside the wavelength region, calculating at the selected waveband a ratio of relative intensities of the first and second fluorescence emissions, and adjusting the relative intensities of the first and second excitation lights to adjust the corresponding first fluorescence emission, second fluorescence emission or both until a suitable calculated ratio is achieved. According to an embodiment, the ratio of relative intensities of the first and second fluorescence emissions may be calculated by dividing an area-under-the curve value corresponding to the first fluorescence emission by an area-under-the curve value corresponding to the second fluorescence emission.

In accordance with another aspect of the invention, there is provided a system for extracting an image of a target fluorophore in a biological material wherein a waveband for the target fluorophore emission overlaps a waveband for autofluorescence emission in the biological material. The system includes a light source configured to illuminate the biological material with a first excitation light to induce a first fluorescence emission arising from both autofluorescence of the biological material and fluorescence of the target fluorophore and with a second excitation light to induce a second fluorescence emission arising from the autofluorescence of the biological material, an image acquisition assembly configured to acquire a first fluorescence image from the first fluorescence emission and a second fluorescence image from the second fluorescence emission, a modulator configured to modulate relative intensities of the first and second excitation lights prior to acquisition of the first and second fluorescence images, and a processor assembly configured to process the first and second fluorescence images to extract a third fluorescence image representing the target fluorophore. According to an embodiment, the light source configured to illuminate the biological material includes an illumination module, the image acquisition assembly includes a fluorescence emission acquisition module, and the processor assembly includes a processor module.

In the embodiments where the target fluorophore is porphyrin, for example, the first excitation light has a wavelength of about 405 nm, the second excitation light has a wavelength of about 450 nm, the selected waveband is about 600 nm, and the calculated ratio is about 1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In accompanying drawings which illustrate embodiments of the invention.

DETAILED DESCRIPTION

Reference will now be made in detail to implementations and embodiments of various aspects and variations of the invention, examples of which are illustrated in the accompanying drawings.

Figure 1:
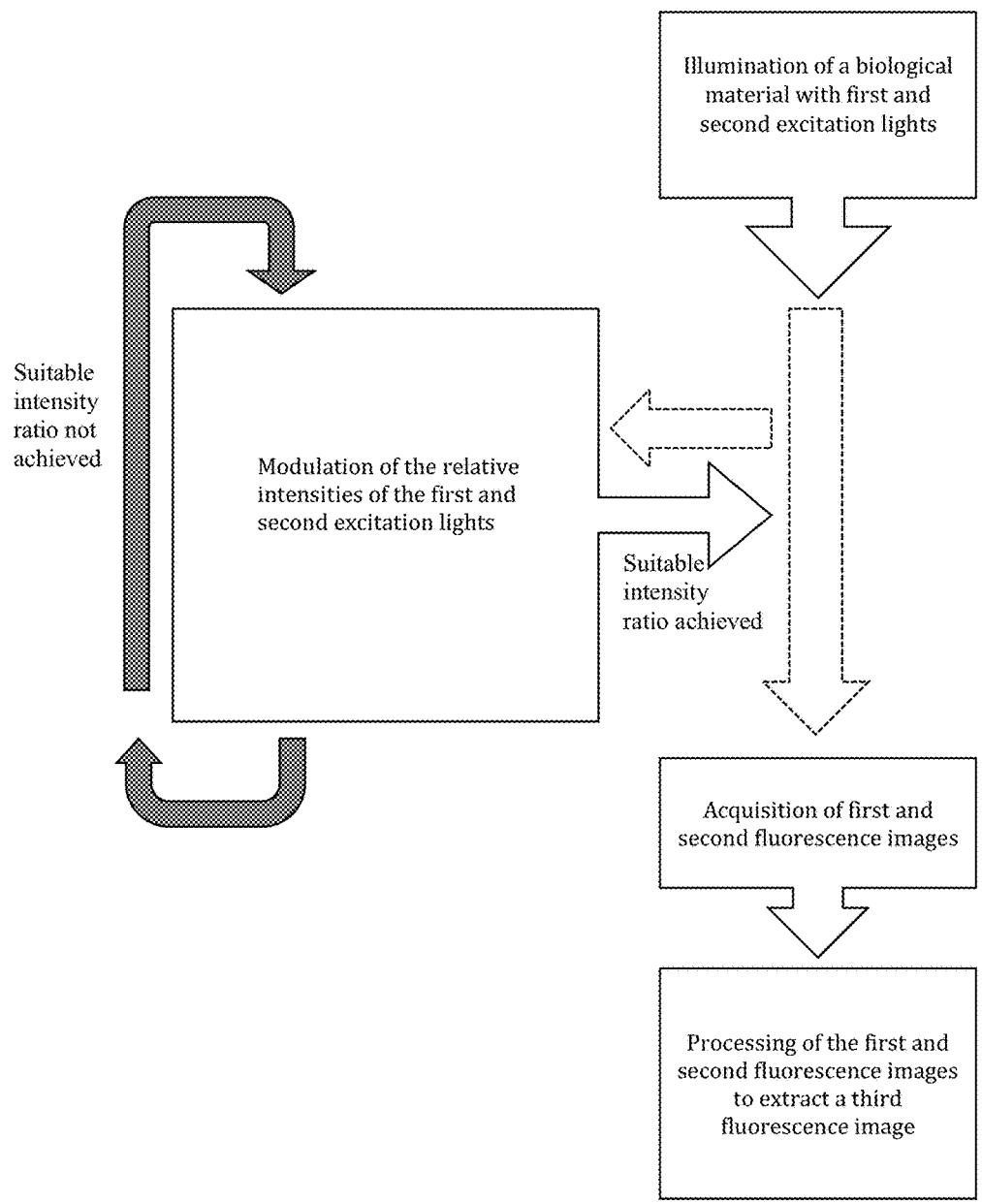
FIG. 1 schematically illustrates an exemplary method according to an embodiment.

According to one aspect of the invention, there is provided a method for extracting an image of a target fluorophore in a biological material wherein a waveband for the target fluorophore emission overlaps a waveband for autofluorescence emission in the biological material. FIG. 1 schematically illustrates the method of the present invention according to an embodiment. Referring to FIG. 1, the method comprises illuminating the biological material with a first excitation light to induce a first fluorescence emission arising from both autofluorescence of the biological material and fluorescence of the target fluorophore and with a second excitation light to induce a second fluorescence emission arising from the autofluorescence of the biological material, acquiring a first fluorescence image from the first fluorescence emission and a second fluorescence image from the second fluorescence emission, and processing the first and second fluorescence images to obtain a third fluorescence image representing the target fluorophore, wherein relative intensities of the first and second excitation lights are modulated prior to acquiring the first and second fluorescence images.

In various embodiments, the biological material includes a material derived from, obtained from, or located in a biological subject (e.g., a mammal), and further includes a material in vitro, in situ or in vivo. Examples of the biological material include a biological tissue or fluid or a fraction thereof, an organ, a cell, a cell line, a cell constituent derived from or located in mammals including humans. The biological material includes a collection of cells obtained from, derived from or in a tissue of the subject such as, for example, epithelium, connective tissue, blood vessels, muscle, nerve tissue, bone from any time in development of the subject. In various embodiments, the biological material includes healthy, diseased, or malignant tissue (e.g., cancerous or tumour tissue) comprising the target fluorophore (e.g., porphyrin). An example of the biological material further includes bacteria, including bacteria present in the subject (human, animal). Examples of the biological material which is a fluid include urine, serum, blood plasma, or blood. In various embodiments, the biological material may be a tissue section used in histochemistry, immunohistochemistry, cytochemistry, immunofluorescence, immunoblotting or other fluorescence-related imaging applications.

In various embodiments, the target fluorophore in the biological material is a fluorophore which when excited by a particular wavelength of light emits a light at a different, typically longer, wavelength. The target fluorophore includes a fluorophore which is of analytical, prognostic, diagnostic, physiological, pathological interest or a combination thereof. In various embodiments, the target fluorophore may be naturally occurring in the biological material (i.e., an endogenous fluorophore), externally administered into the biological material (i.e., an exogenous fluorophore) in a precursor or final form, or a combination thereof. Examples of naturally occurring or endogenous fluorophores include porphyrins, nicotinamide adenine dinucleotide (NAD), elastin, collagen, flavins, and amino acids. In embodiments where a porphyrin is the target fluorophore, the porphyrin includes a class of organic compounds that are in relevant biological systems and are formed as precursor intermediates in the biosynthesis of heme. For example, in humans and other mammals, porphyrins with 8-, 7-, 6-, 5- and 4-carboxyl groups are commonly formed in excess for heme synthesis, and thus are excreted in urine. In various embodiments, the term "porphyrin" includes, for example, porphyrin derivatives, coproporphyrin, uroporphyrin, protoporphyrin, porphyrin conjugates, liposomes, and nanovesicles.

Examples of exogenous fluorophores include various fluorescent probes or fluorescence inducing agents which may be used to augment (e.g., enhance) or provide fluorescent properties to a component of the biological material. For example, a fluorescent probe may associate with or attach to the component of the biological material to, for example, enhance fluorescence of an endogenous fluorophore in the component. Examples of exogenous fluorescent probes include fluorescein isothiocyanate (FITC), fluorescein, a fluorescent dye, 4',6-diaminidino-2-phenylindole (DAPI), and eosin. An example of a fluorescence inducing agent includes a gene which may be inserted into a cell chromosome to induce the production of fluorescent proteins (e.g., green fluorescent protein). The fluorescence inducing agent may be an adjuvant that can augment the fluorescence response of the target fluorophore. For example, in embodiments where the target fluorophore is porphyrin, the adjuvant may be a selected food source (e.g., porphyrinogenic foods or chemicals), aminolevulinic acid or inhibitors of certain enzymes in the HEME pathway (e.g., ferrochelatease inhibitors) which when consumed or administered to the subject, increase the fluorescence response of porphyrin.

The biological material naturally fluoresces or "autofluoresces" in the absence of exogenously administered fluorophores due to the presence of various endogenous fluorophores in the biological material. Autofluorescence originates from various fluorophores in the biological material, including for example nicotinamide adenine dinucleotide (NAD), elastin, collagen, flavins, amino acids, lipofuscins, advanced glycation end-products, and porphyrins. The biological material includes a material that has been processed or otherwise treated prior to being used in the various embodiments of the method and system of the invention. For example, in certain embodiments, pre-treatment may involve photo bleaching of the biological material to reduce the autofluorescence of the biological material presumably by inactivating some of the autofluorescent endogenous fluorophores, and thus facilitating clearer subsequent resolution of the target fluorophore in cases where the target fluorophore is comparatively less susceptible to photobleaching or photobleaches at a slower rate than autofluorescent fluorophores in the biological material.

In accordance with the various embodiments, the method comprises illuminating the biological material with a first excitation light to induce a first fluorescence emission arising from both autofluorescence of the biological material and fluorescence of the target fluorophore, and with a second excitation light to induce a second fluorescence emission arising from the autofluorescence of the biological material. In various embodiments, the wavelength of the first excitation light is selected such that when the first excitation light illuminates the biological material, the fluorophores in the biological material which give rise to autofluorescence and the target fluorophore are both excited and emit a first fluorescence emission. In various embodiments, the wavelength of the second excitation light is selected such that only the fluorophores in the biological material giving rise to autofluorescence are excited and emit a second fluorescence emission. In various embodiments, for example, the first excitation light may have a wavelength ranging from about 350 nm to about 450 nm and the second excitation light may have a wavelength ranging from about 450 nm to about 700 nm. Illumination of the biological material with the first excitation light and the second excitation light includes intermittent illumination, continuous illumination or a combination thereof.

Figure 2A:
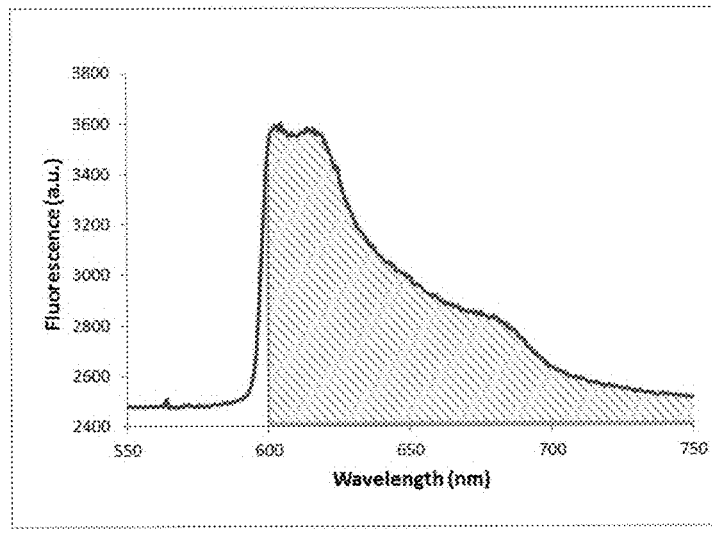
FIGS. 2A-2C illustrates fluorescence spectra arising from autofluorescence and porphyrin in urine (FIG. 2A), autofluorescence (FIG. 2B) in urine, and the differential spectrum corresponding to porphyrin alone obtained in accordance with the various embodiments (FIG. 2C)
Figure 2B:
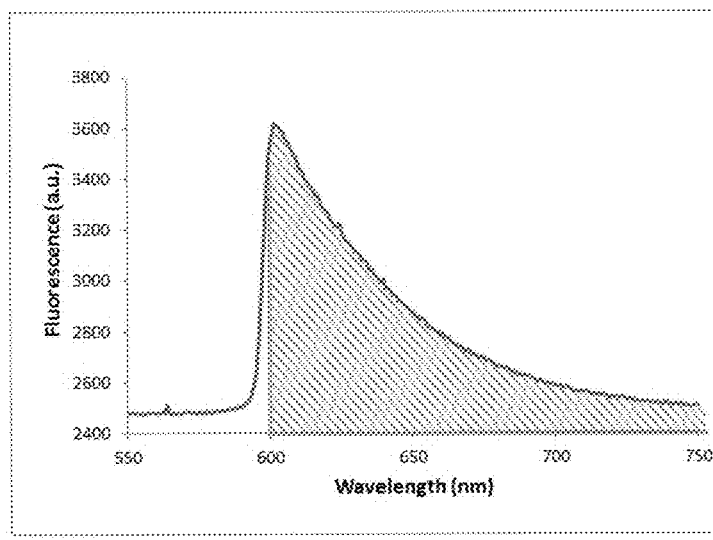
Figure 2C:
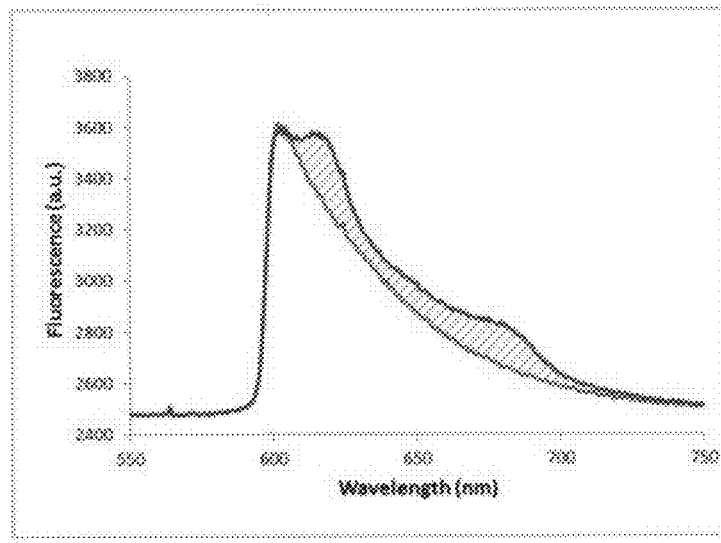
Figure 3A:
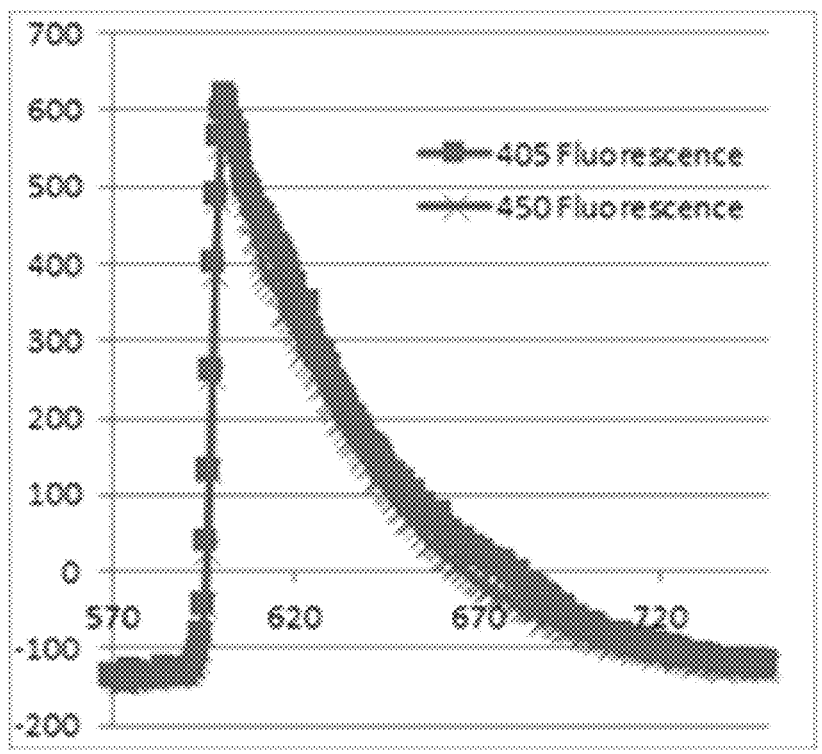
FIGS. 3A-3B illustrates fluorescence spectra of freshly obtained urine (3A) and photobleached urine (3B) at 405 nm and 450 nm according to an embodiment.
Figure 3B:
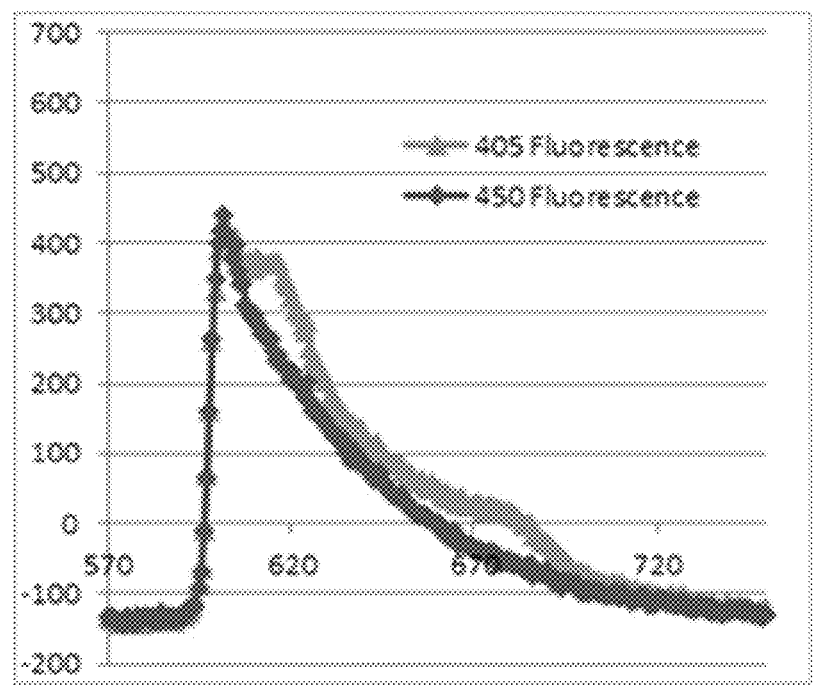

In the embodiment where the target fluorophore is porphyrin, the first excitation light has a wavelength of about 405 nm, and the second excitation light has a wavelength of about 450 nm. FIGS. 2A-2C (shaded areas) illustrates data obtained from porphyrin in urine. In particular, FIG. 2A is a first fluorescence emission spectrum arising from both autofluorescence and porphyrin in urine, and FIG. 2B is a second fluorescence emission spectrum arising from autofluorescence only. FIG. 2C is the differential spectrum corresponding to porphyrin only. In the examples illustrated in FIGS. 2A-2C, the urine was pretreated by photobleaching to facilitate a better discrimination of porphyrin from autofluorescence. In particular, photobleaching pre-treatment was conducted by illuminating the urine with the second excitation light of a wavelength of about 450 nm for about 3 minutes, which resulted in improved discrimination of the phorphyrin from autofluorescence of urine as compared with untreated urine (FIGS. 3A-3B). FIGS. 3A-3B shows fluorescence spectra from freshly obtained urine (FIG. 3A) and spectra obtained following an approximately 3-minute photobleaching exposure of the urine to light at about 450 nm (FIG. 3B).

Figure 4A:
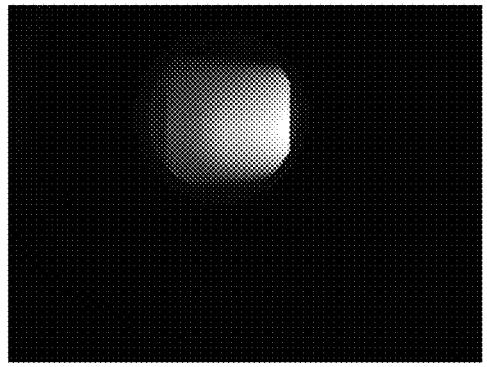
FIGS. 4A-4F illustrates images corresponding to the fluorescence spectra in FIGS. 3A-3B where the left column (FIGS. 4A, 4C, 4E) relates to freshly collected urine, and the right column (FIGS. 4B, 4D, 4F) relates to photobleached urine, the top row (FIGS. 4A, 4B) relates to fluorescence images from excitation at about 405 nm, the middle row (FIGS. 4C, 4D) relates to fluorescence images from excitation at about 450 nm, and the bottom row (FIGS. 4E, 4F) illustrates the differential images corresponding to the target fluorophore (porphyrin) obtained according to an embodiment.
Figure 4B:
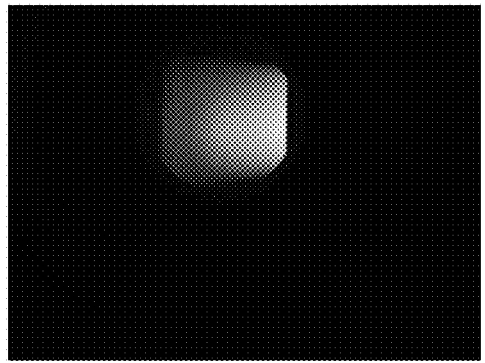
Figure 4C:
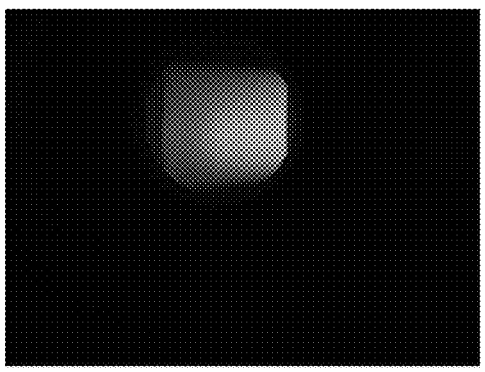
Figure 4D:
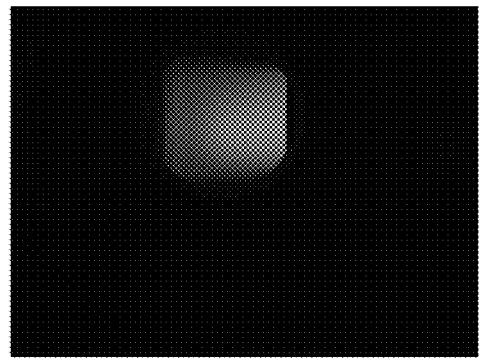
Figure 4E:
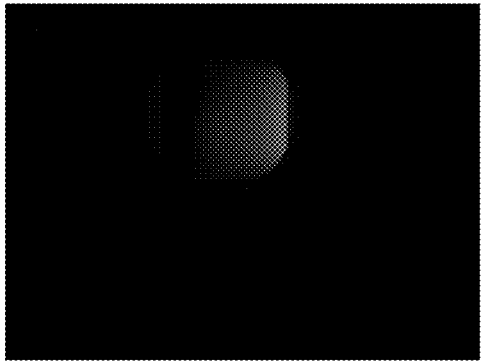
Figure 4F:
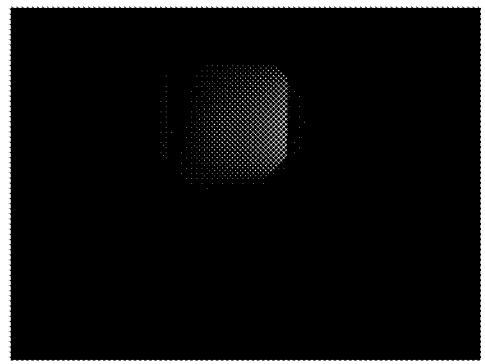

In accordance with the various embodiments, the method comprises acquiring a first fluorescence image from the first fluorescence emission and a second fluorescence image from the second fluorescence emission, and processing the first and second fluorescence images to extract a third fluorescence image representing the target fluorophore wherein the relative intensities of the first and second excitation light are modulated prior to acquiring the first and second fluorescence images. FIGS. 4A to 4D are images corresponding to the spectra in FIGS. 3A-3B acquired when the urine is freshly obtained and when the urine has been exposed to light at about 450 nm for about 3 minutes. FIGS. 4E and 4F are the differential images corresponding to porphyrin only resulting from the processing as described in connection with the various embodiments.

According to an embodiment, modulation of the relative intensities prior to image acquisition comprises identifying a wavelength region in the first and second fluorescence emissions, wherein the wavelength region is a region where emission arising from the fluorophore is present in the first fluorescence emission and absent in the second fluorescence emission, selecting a waveband outside the wavelength region, calculating at the selected waveband a ratio of relative intensities of the first and second fluorescence emissions, and adjusting the relative intensities of the first and second excitation lights to adjust the corresponding first fluorescence emission, second fluorescence emission or both until a suitable calculated ratio is achieved. According to various embodiments a waveband includes a wavelength. For example, in the embodiments where the target fluorophore is porphyrin, as is shown in FIG. 2C or FIG. 3B, the wavelength region where the emission arising from porphyrin is present in the first fluorescence emission and absent in the second fluorescence emission ranges, for example, from about 615 nm to about 625 nm and from about 660 nm to about 700 nm. Therefore, 600 nm was selected as the waveband outside this wavelength region and used as the waveband at which the ratio of the relative intensities at 405 nm and 450 nm was calculated for determining whether adjustment of the relative intensities is needed. In this example, the relative intensities were adjusted until the calculated ratio of about 1 was achieved within +/−2%. In this example, the ratio was calculated at the 600 nm waveband by dividing an area-under-the curve value corresponding to the first fluorescence emission (i.e., the emission arising from excitation at about 405 nm) by an area-under-the curve value corresponding to the second fluorescence emission (i.e., the emission arising from excitation at about 450 nm). In various embodiments, the ratio may be calculated by dividing the intensity at the selected waveband (e.g., a selected wavelength) of the first fluorescence emission by the intensity at the selected waveband (e.g., a selected wavelength) of the second fluorescence emission. In various embodiments, other methods may be used for calculation of the ratio. For example, one or more intensity points in the spectra arising from the respective emissions at 405 nm and 450 nm at the selected waveband (e.g., 600 nm) rather than areas may be used for such a calculation.

In various embodiments, processing comprises subtracting the second fluorescence image from the first fluorescence image to produce an autofluorescence-free image of the target fluorophore (e.g., FIGS. 4E and 4F).

Figure 5A:
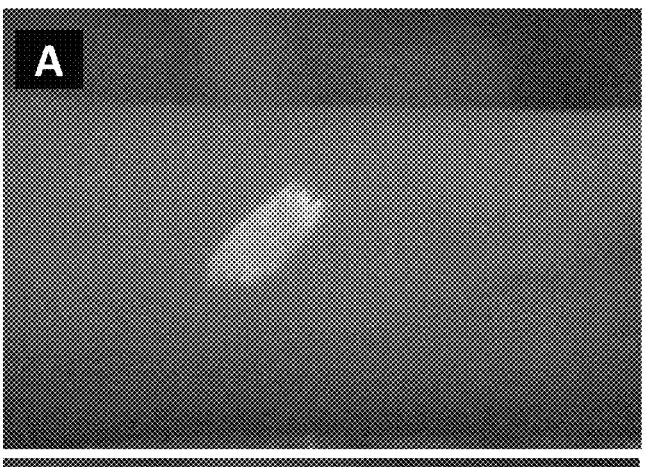
FIG. 5A illustrates an example in vivo fluorescence image of the subject's forearm when excited with 405 nm light, displaying autofluorescence from the forearm and porphyrin fluorescence.
Figure 5B:
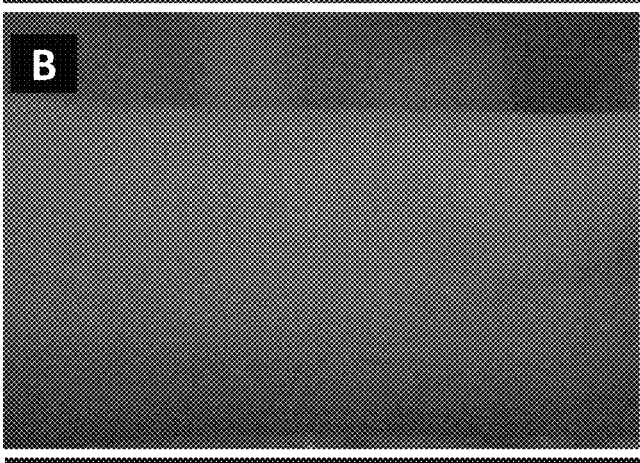
FIG. 5B illustrates a fluorescence image of the same region of the forearm as in FIG. 5A upon excitation with 450 nm light showing a reduction in autofluorescence to a level similar to the autofluorescence level in FIG 5A where the porphyrin fluorescence is absent under the 450 nm excitation.
Figure 5C:
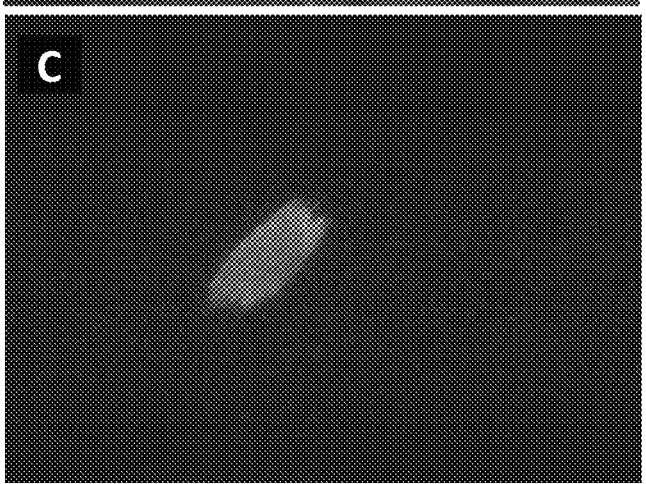
FIG. 5C illustrates a fluorescence image of porphyrin with the autofluorescence removed in accordance with an embodiment.

The methods and systems according to the various embodiments may be used for detecting in situ fluorescence. Experimental data in FIGS. 5A-5C and 6A-6B illustrate example results where porphyrin was applied topically on the skin of a subject. In this example, a porphyrin solution was prepared by dissolving about 0.1 mg of coproporphyrin ester (Sigma-Aldrich) in about 10 mL of dimethyl sulfoxide (DMSO, Sigma Aldrich). The porphyrin solution was applied onto a small area of the subject's forearm using a Q-tip. The fluorescence imaging system used to acquire the data featured a dual-excitation capability at the porphyrin absorption maxima of about 405 nm and about 450 nm. The latter was chosen as the shortest wavelength outside the main porphyrin absorption band, and due to its property to induce high levels of tissue autofluorescence. To ensure that the reflected excitation light does not interfere with the fluorescence images, a 600 nm band pass filter (600 nm±5 nm) was placed in front of the detector in the imaging system, and the excitation intensities at 405 nm and 450 nm were modulated until the ratio of autofluorescence at 450 nm to autofluorescence at 405 nm reached about 1. FIG. 5A is an in vivo fluorescence image of the subject's forearm when excited with 405 nm light displaying autofluorescence from the forearm and porphyrin fluorescence. FIG. 5B is a fluorescence image of the same region of the forearm as in FIG. 5A upon excitation with 450 nm light. Since the autofluorescence induced by 450 nm excitation is greater than the autofluorescence induced by 405 nm excitation, the excitation light at 450 nm was modulated to produce autofluorescence at a level similar to the autofluorescence level in FIG 5A. FIG. 5C illustrates a fluorescence image of porphyrin with the autofluorescence removed in accordance with an embodiment.

FIG. 5A illustrates that the use of single excitation at 405 nm produces a well-localized fluorescence region arising from porphyrin fluorescence. High levels of background in surrounding areas arise from the presence of several endogenous fluorophores in skin (e.g., flavin adenine dinucleotide (FAD), nicotinamide adenine dinucleotide (NAD) and lipids). A similar autofluorescence pattern can also be observed when the same region was excited with different excitation wavelength (450 nm) away from the absorption spectra of porphyrins (FIG. 5B). FIG. 5C shows the resultant image after the processing according to the methods of the present invention where the autofluorescence was successfully attenuated using the method.

Figure 6A:
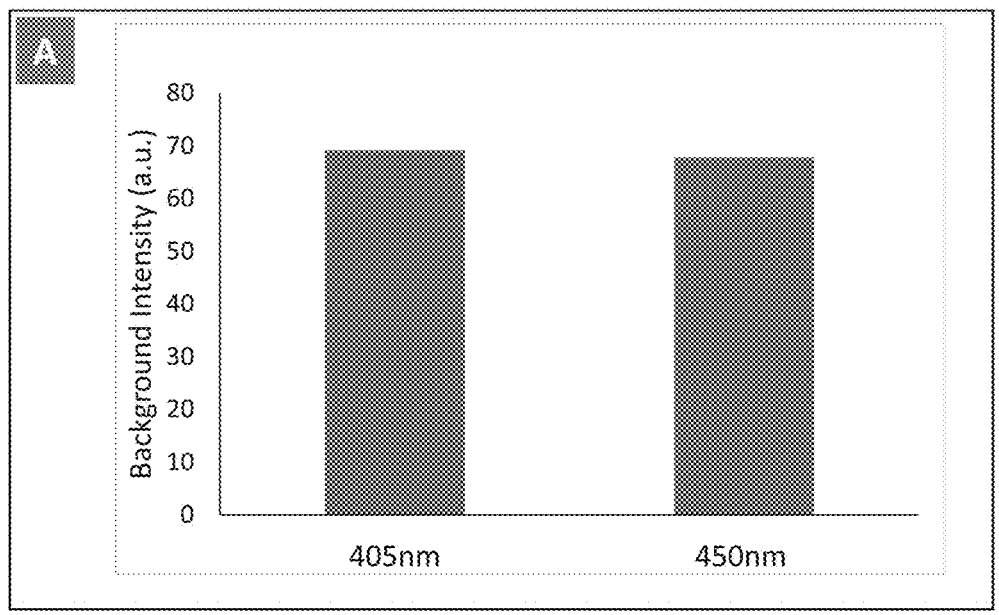
FIG. 6A illustrates background intensity values at 405 nm and 450 nm after the excitation intensities were adjusted at 600 nm, and a lower than about 2% difference between background values was observed between excitations.
Figure 6B:
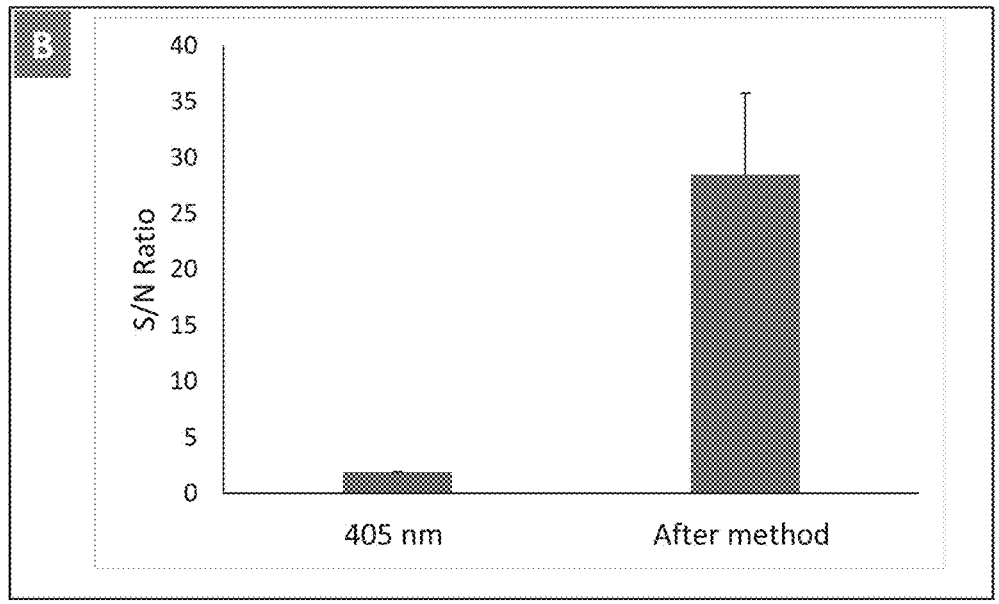
FIG. 6B illustrates a comparison of the signal-to-noise ratio from fluorescence images excited at 405 nm and after background was removed in accordance with an embodiment.

FIG. 6A illustrates background intensity values at 405 nm and 450 nm after the excitation intensities were adjusted at 600 nm, and a lower than about 2% difference between background values was observed between excitations. FIG. 6B illustrates a comparison of the signal-to-noise ratio (S/N Ratio) from fluorescence images excited at 405 nm and after background was removed in accordance with an embodiment. An increase in the S/N Ratio can be achieved using this approach as compared to using single excitation at 405 nm (see FIG. 6B where S/N Ratios of about 28.5 and about 1.9, respectively, are shown).

Various conventional approaches involve simultaneous acquisition of the fluorescence images where all fluorescence species are illuminated, and their fluorescence emissions are collected at the same time. The acquired images are then processed using one or more autofluorescence removal models involving spectral unmixing or background subtraction. Although various conventional approaches have been proposed for removing autofluorescence such, as for example, spectral unmixing (linear decomposition) and digital background subtraction to reveal the differential, such approaches rely on manipulating the images post-acquisition and pre-characterized spectra for autofluorescence, require calibration, and are susceptible to changes in sensitivity based on the concentration of the target fluorophore. While these methods may be cost effective and applicable to both in vitro and in vivo imaging, they are not able to completely remove the autofluorescence component from fluorescence images, and further to account for an instrumental background signal. The modulation of relative intensities of the first and second excitation lights prior to image acquisition, as described in connection with the various embodiments, compensates for relative changes in emission with time due to, for example, different rates of photobleaching between the target fluorophore (e.g., porphyrin) and the fluorophores in the biological material giving rise to autofluorescence. If the modulation of intensities is performed digitally post-image acquisition, as is described in the prior art, the accuracy of the processing of the two images to derive the image of the target fluorophore (e.g., subtraction) is decreased, especially if the magnitude of the first and second fluorescence signals is significantly different. Prior art spectral unmixing methods often require prior knowledge of the amount of autofluorescence in the sample, which may not be constant. In addition, images of the biological material may also include a certain amount of noise or background contributed by the acquisition system itself. Therefore, in contrast to the present invention, normalization of intensities post-image acquisition, as taught in the prior art, is noisier and limited in signal quality especially when the target fluorophore has a low level signal as compared to the autofluorescence signal (e.g., endogenous fluorophores or fluorophores in low-concentration components of the biological material). Furthermore, post-image acquisition amplification of the low level signal of the target fluorophore, as taught in the prior art, also amplifies the instrumental background signal, which further negatively impacts the signal quality. Unlike the prior art approaches, the present invention facilitates dynamic real-time correction for changes in fluorescence in the biological material, and therefore enables a real time representation of the nature of the biological material.

The data generated according to the various embodiments demonstrates that the dual-excitation method of the present invention, as described in connection with the various embodiments, facilitates a reduction in or mitigates the fluorescence background signal during fluorescence imaging of biological tissue by modulating the autofluorescence intensities at a selected wavelength prior to acquisition of fluorescence images. According to the various embodiments, acquisition of spectral images is carried out by timed excitation and light collection from only a target fluorophore of interest or background at a time, This temporal separation of excitation and fluorescence collection minimizes crosstalk. Instead of collecting the emission signal under the same excitation source, the present method according to the various embodiments, induces equivalent background levels by means of a second excitation wavelength (which does not induce fluorescence from the target fluorophore of interest), and then can be subsequently subtracted without decreasing the fluorescence signal from the target fluorophore of interest.

The present method can be beneficial for fluorescence imaging applications where tissue autofluorescence affects fluorescence imaging. The detection of equivalent autofluorescence signatures from different excitation sources facilitates a more accurate molecular diagnosis than a single fluorescence excitation. Moreover, the dual fluorescence imaging approach in accordance with the various embodiments is more robust and accurate than other post-processing analysis techniques since the fluorescence intensity of the fluorophore of interest is not affected by digitally removing the background or modulating the background levels. As is illustrated by the experimental data collected according to an embodiment, this method may be used for the identification of malignant tissues in vivo by exploiting the preferential accumulation of fluorophores such as porphyrins.

In accordance with an aspect of the invention, there is provided a system for extracting an image of a target fluorophore in a biological material. The system comprises a light source configured to illuminate the biological material with a first excitation light to induce a first fluorescence emission arising from both autofluorescence of the biological material and fluorescence of the target fluorophore and with a second excitation light to induce a second fluorescence emission arising from the autofluorescence of the biological material, an image acquisition assembly configured to acquire first fluorescence image from the first fluorescence emission and a second fluorescence image from the second fluorescence emission, a modulator configured to modulate relative intensities of the first and second excitation lights prior to acquisition of the first and second fluorescence images, and a processor assembly configured to process the first and second fluorescence images to extract a third fluorescence image representing the target fluorophore.

Figure 7:
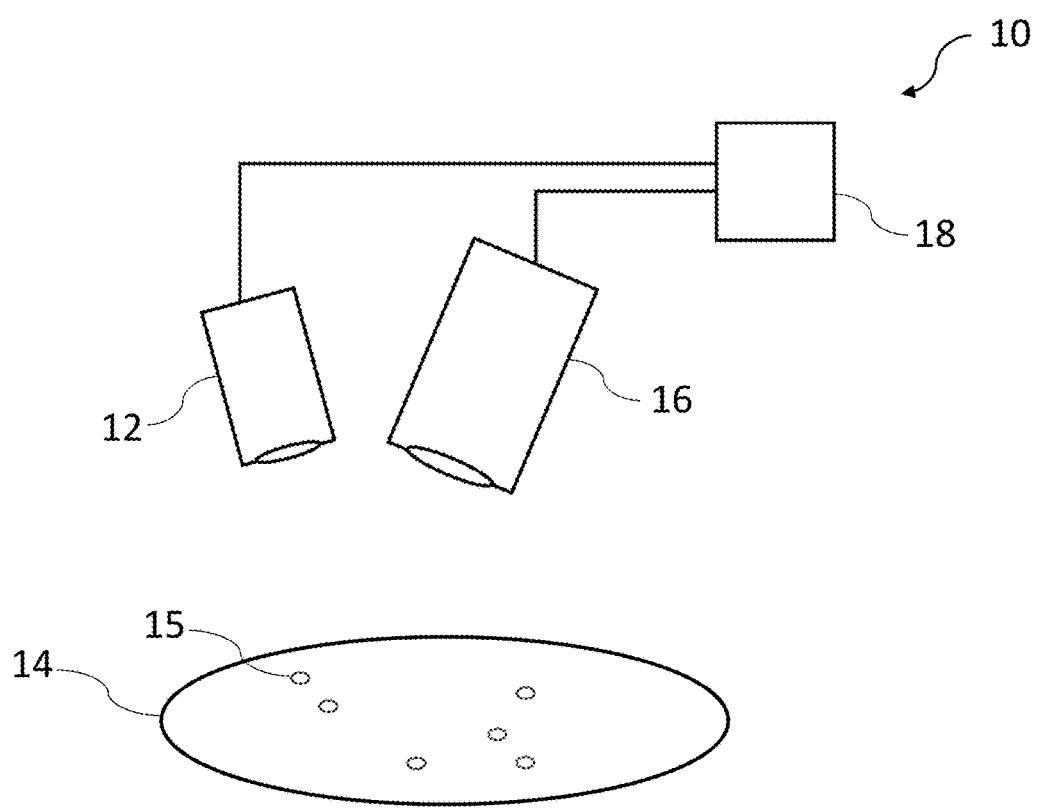
FIG. 7 illustrates a system for extracting an image of a target fluorophore in a biological material according to an embodiment.
Figure 8:
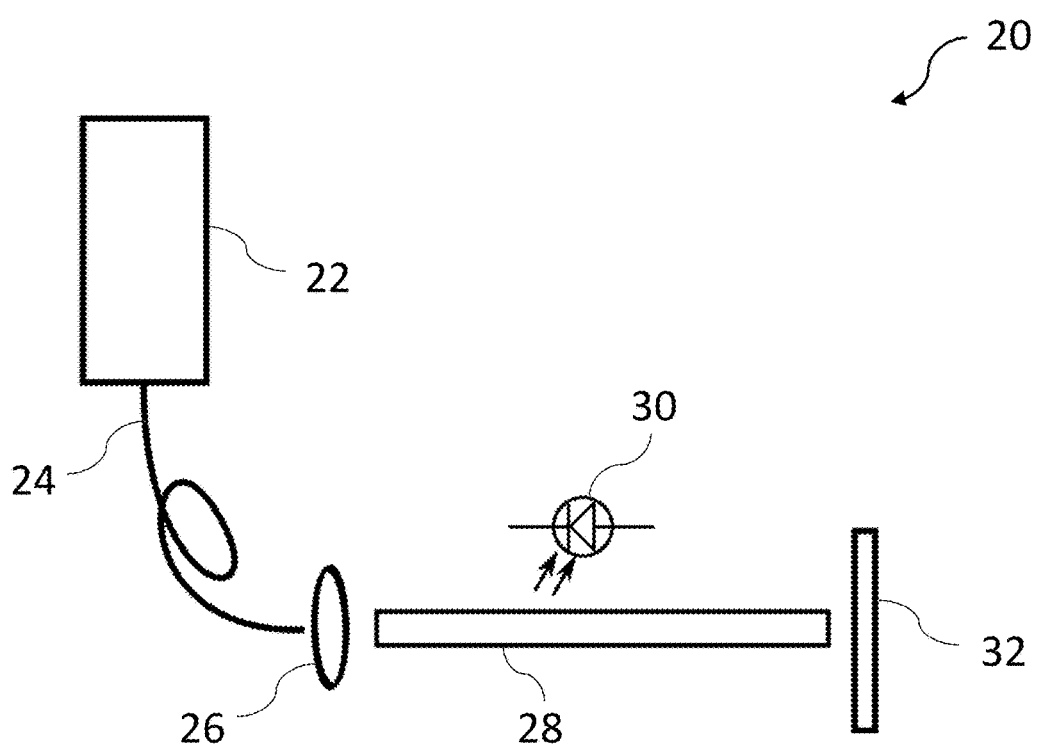
FIG. 8 illustrates an illumination module according to an embodiment.

Selected aspects relating to the system have been described above in connection with the various embodiments of the method of the present invention. Referring to FIG. 7, there is shown an exemplary embodiment of a system 10 for extracting the image of the target fluorophore 15 in the biological material 14. The system 10 comprises the means for illuminating 12 for illumination (e.g., a light source configured to illuminate the biological material) of the biological material 14 with dual fluorescence excitation light, means for acquiring 16 fluorescence images (e.g., an image acquisition assembly configured to acquire fluorescence images) arising from both the autofluorescence and the target fluorophore and from the autofluorescence alone, and means for processing 18 the acquired fluorescence images (e.g., a processor assembly configured to process the acquired images) to extract an image representing only the target fluorophore. In various embodiments, the means for illuminating 12 (e.g., the light source configured to illuminate the biological material) comprises, for example, an illumination module 20 shown in FIG. 8. The illumination module 20 comprises a fluorescence excitation source 22 operatively configured for providing fluorescence excitation having suitable intensities and suitable wavelengths for exciting the target fluorophore and the fluorophores giving rise to autofluorescence. In one embodiment, the fluorescence excitation source 22 may be a single excitation source having dual excitation capabilities for providing a first excitation light for inducing emission arising from both autofluorescence and fluorescence of the target fluorophore, and the second excitation light for inducing emission arising from the autofluoresenee only. In another embodiment, the fluorescence excitation source 22 may comprise two excitation sources (not shown), one for providing the first excitation light and the other for providing the second excitation light. In various embodiments, the fluorescence excitation source 22 includes, for example, a laser diode (which may comprise, for example, one or more fiber-coupled diode lasers), one or more LEDs, arc lamps, or other illuminant technologies of sufficient intensity and appropriate wavelength for providing the first and second excitation lights. In various embodiments, the first and second excitation light from the fluorescence excitation source 22 may be projected through an optical element (i.e., one or more optical elements) to shape and guide the output being used to illuminate the biological sample. The shaping optical element may consist, for example, of one or more lenses, light guides and diffusers. As is illustrated in FIG. 8, the output 24 from the fluorescence excitation source 22 is passed through one or more focusing lenses 26, and then through a homogenizing light pipe 28 such as, for example, light pipes commonly available from Newport Corporation, USA. Finally, the light is passed through an optical diffuser 30 (i.e., one or more optical diffusers or diffractive elements) such as, for example, ground glass diffusers also available from Newport Corporation, USA. Power to the fluorescence excitation source 22 itself is provided by, for example, a high-current laser driver such as those available from Lumina Power Inc., USA. In the embodiment where the fluorescence excitation source 22 is a laser, the laser may be operated in a pulsed mode during the image acquisition process. In this embodiment, an optical sensor such as a solid state photodiode 32 is incorporated into the illumination module 20 and samples the illumination intensity produced by the illumination module 20 via scattered or defuse reflections from the various optical elements.

In an alternative embodiment, the means for illuminating 12 (e.g., the light source) may also be configured to provide an additional functionality such as white light illumination. In another embodiment, the method and system of the present invention may further comprise acquiring and combining the third fluorescence image representing the target fluorophore with a white light image of the biological material. In this manner, the location of the targeted fluorophore can be visualized within the context of the biological material. This is useful in instances in which the biological material cannot be viewed directly with the human eye.

In various embodiments, the illumination module 20 in FIG. 8 comprises means for modulating (not shown) the relative intensities of the first and second excitation lights from the fluorescence excitation source 22 (e.g., a modulator configured to modulate the relative intensities of the first and second excitation lights from the fluorescence excitation source), so as to allow intensity adjustment. Such modulation may include modulation of the power to the light source, mechanical interruption of the light beam by shutters, apertures or choppers, optical, opto-mechanical or electro-optical diversion, filtering or blocking of the light beam or similar modulation.

Figure 9:
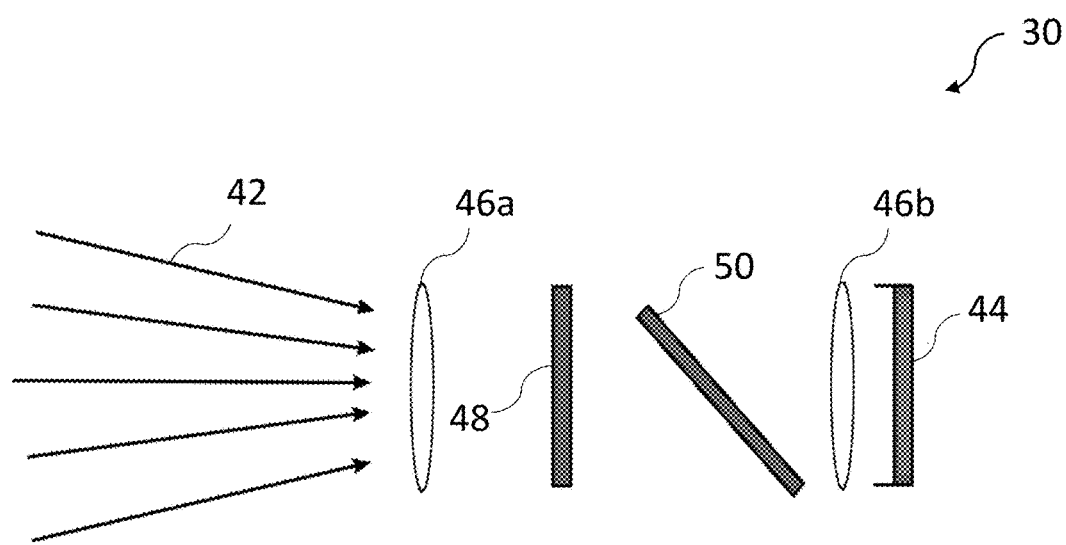
FIG. 9 illustrates a fluorescence emission acquisition module according to an embodiment.

Referring back to FIG. 7, the means for acquiring 16 (e.g., an image acquisition assembly) comprises, for example, a fluorescence emission acquisition module 30 (e.g., a camera module) shown in FIG. 9 for acquiring the first and second fluorescence images. As is shown in FIG. 9, the fluorescence emission 42 from the target fluorophore in the biological material and the fluorescence emission from other fluorophores giving rise to autofluorescence or both is collected and focused onto an image sensor 44 using an arrangement of various optical elements, e.g., 46a, 46b, 48 and 50. The charge that results from the optical signal transduced by the image sensor 44 is converted to a video signal by the appropriate read-out and amplification electronics in the fluorescence emission acquisition module 30.

Referring back to FIG. 7, in various embodiments, the means for processing 18 (e.g., a processor assembly) comprises, for example, a processor module (not shown) for analyzing the emission signals, performing calculations for subtracting the second fluorescence image from the first fluorescence image to output the calculated information to an appropriate display and/or recording device. In various embodiments, the processor module comprises any computer or computing means such as, for example, a tablet, laptop, desktop or networked computer. In various embodiments, the processor module may have a data storage module with the capability to save data (e.g., image sequences) to a tangible non-transitory computer readable medium such as, for example, internal memory, a hard disk, or flash memory, so as to enable recording and/or post-processing of acquired data. In various embodiments, the processor module may have an internal clock to enable control of the various elements and ensure correct timing of illumination and sensor shutters. In various other embodiments, the processor module may also provide user input and graphical display of outputs. The imaging system may optionally be configured with a video display (not shown) to display the images as they are being acquired or played back after recording, or further to visualize the data generated at various stages of the method. In various embodiments, the means for processing (e.g., the processor assembly) is in communication with an imaging system or is a component of the imaging system. An example of the imaging system in accordance with an embodiment is an endoscope.

In operation, and with continuing reference to the embodiments in FIGS. 7 to 9, the biological material is positioned in the illumination path of the means for illuminating 12 (e.g., the light source) of the system 10 comprising the illumination module 20, and such that, for example, the illumination module 20 produces a substantially uniform field of illumination across substantially the entire area of the biological material. The fluorescence excitation source 22 (e.g., the laser diode) is turned on and begins the shutter sequence for the image sensor (e.g., image sensor 44 of the fluorescence emission acquisition module 30). The fluorescence emission from the biological material is collected by the front imaging optics of the fluorescence emission acquisition module 30 such as optics 46a for example in FIG. 9 at the selected waveband (e.g., for porphyrin the selected wavelength is about 600 nm), and a ratio of the relative intensities is calculated. If the calculated ratio is suitable (e.g., for porphyrin, a suitable calculated ratio is in the range of about 0.98 to 1.02), the first and second fluorescence images are acquired. If the ratio is not suitable, the relative intensities of the first and second excitation lights are modulated and re-calculated until the suitable ration is achieved. The obtained first and second fluorescence images are then subtracted to extract a third fluorescence image representing only the target fluorophore.

According to another aspect of the invention, there is provided a tangible non-transitory computer readable medium having computer-executable (readable) program code embedded thereon comprising a method for extracting an image of a target fluorophore in a biological material wherein a waveband for the target fluorophore emission overlaps a waveband for autofluorescence emission in the biological material, the method comprising:

illuminating the biological material with a first excitation light to induce a first fluorescence emission arising from both autofluorescence of the biological material and fluorescence of the target fluorophore and with a second excitation light to induce a second fluorescence emission arising from the autofluorescence of the biological material;

acquiring a first fluorescence image from the first fluorescence emission and a second fluorescence image from the second fluorescence emission; and processing the first and second fluorescence images to extract a third fluorescence image representing the target fluorophore, wherein relative intensities of the first and second excitation lights are modulated prior to acquiring the first and second fluorescence images.

One skilled in the art will appreciate that program code according to the various embodiments can be written in any appropriate programming language and delivered to the processor in many forms, including, for example, but not limited to information permanently stored on non-writeable storage media (e.g., read-only memory devices such as ROMs or CD-ROM disks), information alterably stored on writeable storage media (e.g., hard drives), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

In yet further aspects, there is provided a kit including the system and the exogenous fluorophore as described in connection with the various embodiments.

Therefore, the various embodiments of the invention facilitate discrimination of the fluorescence of interest from an unknown combination of autofluorescence and fluorescence of interest. The present invention facilitates improvements in image quality for target fluorophores, preserves signal fluorescence while eliminating autofluorescence as well as background, and increases the resulting signal to autofluorescence ratio and the overall sensitivity of detection. The present invention is adaptable to a wide array of biological materials, and may be applied to any fluorescence imaging application. The present invention may be used to image and analyze a biological sample to discern the presence, absence, concentration, and/or spatial distribution of one of more fluorophore targets in the biological material. The present invention may be further used as a complementary tool for medical assessment or biological assessment (e.g., assessment of a biological phenomenon), diagnostic assessment, therapeutic assessment, physiological assessment, or a combination thereof.

While the present invention has been illustrated and described in connection with various embodiments shown and described in detail, it is not intended to be limited to the details shown, since various modifications and structural changes may be made without departing in any way from the scope of the present invention. Various modifications of form, arrangement of components, steps, details and order of operations of the embodiments illustrated, as well as other embodiments of the invention may be made without departing in any way from the scope of the present invention, and will be apparent to a person of skill in the art upon reference to this description. It is therefore contemplated that the appended claims will cover such modifications and embodiments as they fall within the true scope of the invention. For the terms "for example" and "such as," and grammatical equivalences thereof, the phrase "and without limitation" is understood to follow unless explicitly stated otherwise. As used herein, the singular forms "a," "an," and "the" include plural referents unless the context clearly dictates otherwise.

What is claimed is:

1. A method for extracting an image of a target fluorophore in a biological material wherein a waveband for the target fluorophore emission overlaps a waveband for autofluorescence emission in the biological material, the method comprising:
    illuminating the biological material with a first excitation light to induce a first fluorescence emission arising from both autofluorescence of the biological material and fluorescence of the target fluorophore and with a second excitation light to induce a second fluorescence emission arising from the autofluorescence of the biological material;
    acquiring a first fluorescence image from the first fluorescence emission and a second fluorescence image from the second fluorescence emission; and
    processing the first and second fluorescence images to extract a third fluorescence image representing the target fluorophore, wherein relative intensities of the first and second excitation lights are modulated prior to acquiring the first and second fluorescence images.

2. The method of claim 1 wherein the modulation of the relative intensities comprises:
    identifying a wavelength region in the first and second fluorescence emissions, wherein the wavelength region is a region where emission arising from the fluorophore is present in the first fluorescence emission and absent in the second fluorescence emission;
    selecting a waveband outside the wavelength region;
    calculating at the selected waveband a ratio of relative intensities of the first and second fluorescence emissions; and
    adjusting the relative intensities of the first and second excitation lights to adjust the corresponding first fluorescence emission, second fluorescence emission or both until a suitable calculated ratio is achieved.

3. The method of claim 2 wherein the waveband outside the wavelength region comprises one or more wavelengths in fluorescence spectra arising from the first and second fluorescence emissions.

4. The method of claim 2 wherein calculating the ratio of relative intensities of the first and second fluorescence emissions comprises dividing an area-under-the curve value corresponding to the first fluorescence emission by an area-under-the curve value corresponding to the second fluorescence emission.

5. The method of claim 1 wherein the first excitation light has a wavelength of about 405 nm and the second excitation light has a wavelength of about 450 nm when the target fluorophore is porphyrin.

6. The method of claim 2 wherein the selected waveband is about 600 nm and wherein the calculated ratio is about 1.

7. The method of claim 1 wherein processing the first and second fluorescence images to extract the third fluorescence image representing the target fluorophore comprises subtracting the second fluorescence image from the first fluorescence image.

8. The method of claim 1 wherein the biological material is pretreated by photobleaching.

9. The method of claim 1 wherein the target fluorophore is endogenous, exogenous, or a combination thereof.

10. The method of claim 9 wherein the endogenous fluorophore is porphyrin, a porphyrin precursor, a porphyrin analog, a porphyrin derivative, a porphyrin conjugate, a porphyrin liposome, a porphyrin nanovesicle, or a combination thereof.

11. The method of claim 10 wherein the porphyrin comprises a coproporphyrin, a uroporphyrin, a protoporphyrin, or a combination thereof.

12. The method of claim 9 wherein the exogenous fluorophore is a fluorescent dye, a fluorescence inducing agent, or a combination thereof.

13. Use of the method of claim 1 in hystochemistry, cytochemistry, or a combination thereof.

14. A system for extracting an image of a target fluorophore in a biological material wherein a waveband for the target fluorophore emission overlaps a waveband for autofluorescence emission in the biological material, the system comprising:
    a light source configured to illuminate the biological material with a first excitation light to induce a first fluorescence emission arising from both autofluorescence of the biological material and fluorescence of the target fluorophore and with a second excitation light to induce a second fluorescence emission arising from the autofluorescence of the biological material;
    an image acquisition assembly configured to acquire a first fluorescence image from the first fluorescence emission and a second fluorescence image from the second fluorescence emission;
    a modulator configured to modulate relative intensities of the first and second excitation lights prior to acquisition of the first and second fluorescence images; and
    a processor assembly configured to process the first and second fluorescence images to extract a third fluorescence image representing the target fluorophore.

15. The system of claim 14 wherein the modulator configured to modulate the relative intensities comprises:
    means for identifying a wavelength region in the first and second fluorescence emissions, wherein the wavelength region is a region where emission arising from the fluorophore is present in the first fluorescence emission and absent in the second fluorescence emission;
    means for selecting a waveband outside the wavelength region;

means for calculating at the selected waveband a ratio of relative intensities of the first and second fluorescence emissions; and means for adjusting the relative intensities of the first and second excitation lights to adjust the corresponding first fluorescence emission, second fluorescence emission or both until a suitable calculated ratio is achieved.

16. The system of claim 15 wherein the waveband outside the wavelength region comprises one or more wavelengths in fluorescence spectra arising from the first and second fluorescence emissions.

17. The system of claim 15 wherein means for calculating the ratio of relative intensities of the first and second fluorescence emissions comprises means for dividing an area-under-the curve value corresponding to the first fluorescence emission by an area-under-the curve value corresponding to the second fluorescence emission.

18. The system of claim 14 wherein the first excitation light has a wavelength of about 405 nm and the second excitation light has a wavelength of about 450 nm when the target fluorophore is porphyrin.

19. The system of claim 15 wherein the selected waveband is about 600 nm and wherein the calculated ratio is about 1.

20. The system of claim 14 wherein the processor assembly configured to process the first and second fluorescence images to extract the third fluorescence image representing the target fluorophore comprises means for subtracting the second fluorescence image from the first fluorescence image.

21. The system of claim 14 wherein the light source configured to illuminate the biological material comprises an illumination module comprising a fluorescence excitation source, the fluorescence excitation source operatively configured to generate the first and second excitation lights.

22. The system of claim 21 wherein the illumination module further comprises an optical element operatively configured to shape and guide the first and second excitation lights exiting the illumination module.

23. The system of claim 22 wherein the optical element comprises a lens, a light guide, a diffuser, or a combination thereof.

24. The system of claim 14 wherein the image acquisition assembly comprises a fluorescence emission acquisition module, the fluorescence emission acquisition module comprising an image sensor.

25. The system of claim 24 wherein the fluorescence emission acquisition module further comprises an optical element disposed in front of the image sensor operatively configured to capture, filter, and direct the first and second fluorescence emissions.

26. The system of claim 14 wherein the processor assembly comprises a processor module.

27. The system of claim 26 wherein the processor module is operatively configured to control an operation of the light source, to control an operation of the image acquisition assembly, or a combination thereof.

28. The system of claim 14 wherein the biological material is pretreated by photobleaching.

29. The system of claim 14 wherein the target fluorophore is endogenous, exogenous, or a combination thereof.

30. The system of claim 29 wherein the endogenous fluorophore is porphyrin, a porphyrin precursor, a porphyrin analog, a porphyrin derivative, a porphyrin conjugate, a porphyrin liposome, a porphyrin nanovesicle, or a combination thereof.

31. The system of claim 30 wherein the porphyrin comprises a coproporphyria a uroporphyrin, a protoporphyrin, or a combination thereof.

32. The system of claim 29 wherein the exogenous fluorophore is a fluorescent dye, a fluorescence inducing agent, or a combination thereof.

33. The method of claim 1, wherein the biological material comprises a biological tissue, a biological fluid, or a fraction thereof.

34. The method of claim 1, wherein the biological material comprises an organ, a cell, a cell line, a cell constituent derived from or located in a mammal.

35. The method of claim 1, wherein the biological material comprises healthy, diseased or malignant tissue.

36. The method of claim 1, wherein the biological material comprises a tissue section for use in histochemistry, immunohistochemistry, cytochemistry, immunofluorescence, immunoblotting, or a fluorescence-related imaging application.

* * * * *